US008754015B2

(12) United States Patent
Dewhurst et al.

(10) Patent No.: US 8,754,015 B2
(45) Date of Patent: Jun. 17, 2014

(54) MODIFIED PHAGE FOR DISPLAYING POST-TRANSLATIONALLY MODIFIED PROTEINS AND USES THEREOF

(75) Inventors: Stephen Dewhurst, Rochester, NY (US); John J. Treanor, Rochester, NY (US)

(73) Assignee: University of Rochester, Rochester, NY (US)

( * ) Notice: Subject to any disclaimer, the term of this patent is extended or adjusted under 35 U.S.C. 154(b) by 1063 days.

(21) Appl. No.: 12/514,903

(22) PCT Filed: Nov. 20, 2007

(86) PCT No.: PCT/US2007/085214

§ 371 (c)(1), (2), (4) Date: May 14, 2009

(87) PCT Pub. No.: WO2008/115296

PCT Pub. Date: Sep. 25, 2008

(65) Prior Publication Data

US 2010/0284967 A1 Nov. 11, 2010

Related U.S. Application Data

(60) Provisional application No. 60/866,710, filed on Nov. 21, 2006.

(51) Int. Cl.
*C40B 50/06* (2006.01)

(52) U.S. Cl.
USPC ............................................................ 506/26

(58) Field of Classification Search
None
See application file for complete search history.

(56) References Cited

U.S. PATENT DOCUMENTS 5,679,510 A 10/1997 Ray et al.

OTHER PUBLICATIONS

Sathaliyawala et al. (Aug. 2006) Journal of Virology vol. 80 pp. 7688 to 7698.*
Dunn (Oct. 1996) Biochimie vol. 78 pp. 856 to 861.*
Tong et al., 2005 Immunogenicity and safety of an adjuvanted hepatitis B vaccine in pre-hemodialysis and hemodialysis patients. Kidney Int 68:2298-303.
Tran et al., 2004. Avian influenza A (H5N1) in 10 patients in Vietnam. N Engl J Med 350:1179-88.
Treanor et al., 1996. Evaluation of a recombinant hemagglutinin expressed in insect cells as an influenza vaccine in young and elderly adults. J Infect Dis 173:1467-70.
Treanor et al., 2006. Safety and immunogenicity of an inactivated subvirion influenza A (H5N1) vaccine. N Engl J Med 354:1343-51.
Treanor et al., 2006. Dose-related safety and immunogenicity of a trivalent baculovirus-expressed influenza-virus hemagglutinin vaccine in elderly adults. J Infect Dis 193:1223-8.
Treanor et al., 1990. Passively transferred monoclonal antibody to the M2 protein inhibits influenza A virus replication in mice. J Virol 64:1375-7.

(Continued)

*Primary Examiner* — Ardin Marschel
*Assistant Examiner* — Christian Boesen
(74) *Attorney, Agent, or Firm* — Kilpatrick Townsend & Stockton, LLP

(57) ABSTRACT

Disclosed herein are modified phage comprising a fusion protein located on the surface of the phage wherein the fusion protein comprises a surface protein and a post-translationally modified protein. Also disclosed are methods of making and using modified phage comprising post-translationally modified proteins located on the surface of the phage.

1 Claim, 7 Drawing Sheets gpD- Procapsid

EDTA Sens.

gpD Fusion Protein *(Eukaryotic cell-derived)*

Mature gpD+ Capsid

EDTA Res.

(56) References Cited

OTHER PUBLICATIONS

Treanor et al., 2001. Safety and immunogenicity of a recombinant hemagglutinin vaccine for H5 influenza in humans. Vaccine 19:1732-7.
Uchiyama et al., 2005. Designing scaffolds of peptides for phage display libraries Journal of Bioscience and Bioengineering 99(5):448-456.
Ungchusak et al., 2005. Probable person-to-person transmission of avian influenza A (H5N1). N Engl J Med 352:333-40.
Verthelyi et al., 2004. CpG oligodeoxynucleotides improve the response to hepatitis B immunization in healthy and SIV-infected rhesus macaques. Aids 18:1003-8.
Villa et al., 2005. Prophylactic quadrivalent human papillomavirus (types 6, 11, 16, and 18) L1 virus-like particle vaccine in young women: a randomised double-blind placebo-controlled multicentre phase II efficacy trial. Lancet Oncol 6:271-8.
Wang et al., 2003. Cellular immune responses to helper-free HSV-1 amplicon particles encoding HIV-1 gp120 are enhanced by DNA priming. Vaccine 21:2288-97.
Wang et al., 2006. Expression and purification of an influenza hemagglutinin—one step closer to a recombinant protein-based influenza vaccine. Vaccine 24:2176-85.
Webby et al., 2004. Responsiveness to a pandemic alert: use of reverse genetics for rapid development of influenza vaccines. Lancet 363:1099-103.
Weeratna, R., L. Comanita, and H. L. Davis. 2003. CPG ODN allows lower dose of antigen against hepatitis B surface antigen in BALB/c mice. Immunol Cell Biol 81:59-62.
Wei et al., 2003. Antibody neutralization and escape by HIV-1. Nature 422:307-12.
Wille-Reece et al., 2006. Toll-like receptor agonists influence the magnitude and quality of memory T cell responses after prime-boost immunization in nonhuman primates. J Exp Med 203:1249-58.
Wyatt et al., 1998. The antigenic structure of the HIV gp120 envelope glycoprotein. Nature 393:705-11.
Yang et al., 2000. Novel fold and capsid-binding properties of the lambda-phage display platform protein gpD. Nat Struct Biol 7:230-7.
Yang et al., 2000. Characterization of stable, soluble trimers containing complete ectodomains of human immunodeficiency virus type 1 envelope glycoproteins. J Virol 74:5716-25.
Yang et al., 2000. Modifications that stabilize human immunodeficiency virus envelope glycoprotein trimers in solution. J Virol 74:4746-54.
Yang et al., 2002. Highly stable trimers formed by human immunodeficiency virus type 1 envelope glycoproteins fused with the trimeric motif of T4 bacteriophage fibritin. J Virol 76:4634-42.
Yang, X., R. Wyatt, and J. Sodroski. 2001. Improved elicitation of neutralizing antibodies against primary human immunodeficiency viruses by soluble stabilized envelope glycoprotein trimers. J Virol 75:1165-71.
Zanghi et al., 2005. A simple method for displaying recalcitrant proteins on the surface of bacteriophage lambda. Nucleic Acids Res 33:e160.
Zhang et al., 2005. Endotoxin removal using a synthetic adsorbent of crystalline calcium silicate hydrate. Biotechnol Prog 21:1220-5.
Zhang et al., 2003. Effectiveness of the quillaja saponin semi-synthetic analog GPI-0100 in potentiating mucosal and systemic responses to recombinant HagB from *Porphyromonas gingivalis*. Vaccine 21:4459-71.
Zhen et al., 2004. Transient overexpression of kappa and mu opioid receptors using recombinant adenovirus vectors. J Neurosci Methods 136:133-9.
Zhu et al., 2006. Distribution and three-dimensional structure of AIDS virus envelope spikes. Nature 441:847-52.
Zolla-Pazner, S. 2004. Identifying epitopes of HIV-1 that induce protective antibodies. Nat Rev Immunol 4:199-210.
Zwick et al., 2001. Identification and characterization of a peptide that specifically binds the human, broadly neutralizing anti-human immunodeficiency virus type 1 antibody b12. J Virol 75:6692-9.
Maurer et al., 2005. A therapeutic vaccine for nicotine dependence: preclinical efficacy, and Phase I safety and immunogenicity. Eur J Immunol 35:2031-40.
McAleer et al., 1984. Human hepatitis B vaccine from recombinant yeast. Nature 307:178-80.
McGuire et al., 2004. A library-selected, Langerhans cell-targeting peptide enhances an immune response. DNA Cell Biol 23:742-52.
Merril et al., 2003. The prospect for bacteriophage therapy in Western medicine. Nat Rev Drug Discov 2:489-97.
Mikawa et al., 1996. Surface display of proteins on bacteriophage lambda heads. J. Mol. Biol. 262:21-30.
Monaci et al., 2001. Phage as gene delivery vectors. Curr Opin Mol Ther 3:159-69.
Moore et al., 2001. Genetic subtypes, humoral immunity, and human immunodeficiency virus type 1 vaccine development. J Virol 75:5721-9.
Murialdo, H., and P. N. Ray. 1975. Model for arrangement of minor structural proteins in head of bacteriophage lambda. Nature 257:815-7.
Mossadegh et al., 2004. Codon optimization of the human papillomavirus 11 (HPV 11) L1 gene leads to increased gene expression and formation of virus-like particles in mammalian epithelial cells. Virology 326:57-66.
Nabel, G. J., and N. J. Sullivan. 2000. Antibodies and resistance to natural HIV infection. N Engl J Med 343:1263-5.
Neirynck et al., 1999. A universal influenza A vaccine based on the extracellular domain of the M2 protein. Nat Med 5:1157-63.
Ni et al., 2006. Toward a carbohydrate-based HIV-1 vaccine: synthesis and immunological studies of oligomannose-containing glycoconjugates. Bioconjug Chem 17:493-500.
Nwe et al., 2006. Expression of hemagglutinin protein from the avian influenza virus H5N1 in a baculoviruslinsect cell system significantly enhanced by suspension culture. BMC Microbiol 6:16.
Ochs et al., 1992. Antibody responses to bacteriophage phi X174 in patients with adenosine deaminase deficiency. Blood 80:1163-71.
Ochs et al., 1971. Immunologic responses to bacteriophage phi-X 174 in immunodeficiency diseases. J Clin Invest 50:2559-68.
Olsen et al., 2006. Global patterns of influenza a virus in wild birds. Science 312:384-8.
Pantophlet, R., and D. R. Burton. 2006. GP120: target for neutralizing HIV-1 antibodies. Annu Rev Immunol 24:739-69.
Parrott et al., 2003. Metabolically biotinylated adenovirus for cell targeting, ligand screening, and vector purification. Mol Ther 8:688-700.
Pashov et al., 2005. Antigenic properties of peptide mimotopes of HIV-1-associated carbohydrate antigens. J Biol Chem 280:28959-65.
Pashov et al., 2006. Multiple antigenic mimotopes of HIV carbohydrate antigens—relating structure and antigenicity. J Biol Chem. 281(40):29675-29683.
Petsch, D., and F. B. Anspach. 2000. Endotoxin removal from protein solutions. J Biotechnol 76:97-119.
Piersanti et al., 2004. Mammalian cell transduction and internalization properties of lambda phages displaying the full-length adenoviral penton base or its central domain. J Mol Med 82:467-76.
Poignard et al., 2003. Heterogeneity of envelope molecules expressed on primary human immunodeficiency virus type 1 particles as probed by the binding of neutralizing and nonneutralizing antibodies. J Virol 77:353-65.
Powers et al., 1995. Influenza A virus vaccines containing purified recombinant H3 hemagglutinin are well tolerated and induce protective immune responses in healthy adults. J Infect Dis 171:1595-9.
Reichelt, P., C. Schwarz, and M. Donzeau. 2006. Single step protocol to purify recombinant proteins with low endotoxin contents. Protein Expr Purif 46:483-8.
Ren, Z., and L. W. Black. 1998. Phage T4 SOC and HOC display of biologically active, full-length proteins on the viral capsid. Gene 215:439-44.
Richards et al., 2003. Engineered fibronectin type III domain with a RGDWXE sequence binds with enhanced affinity and specificity to human alphavbeta3 integrin. J Mol Biol 326:1475-88.

(56) References Cited

OTHER PUBLICATIONS

Richardson et al., 2002. Immunogenicity of HIV-1 IIIB and SHIV 89.6P Tat and Tat toxoids in rhesus macaques: induction of humoral and cellular immune responses. DNA Cell Biol 21:637-51.
Rizzuto et al., 1998. A conserved HIV gp120 glycoprotein structure involved in chemokine receptor binding. Science 280:1949-53.
Rose et al., 1999. Oral vaccination of mice with human papillomavirus virus-like particles induces systemic virus-neutralizing antibodies. Vaccine 17:2129-35.
Ross et al., 2001. Enhanced avidity maturation of antibody to human immunodeficiency virus envelope: DNA vaccination with gp120-C3d fusion proteins. AIDS Res Hum Retroviruses 17:829-35.
Rowe et al., 1999. Detection of antibody to avian influenza A (H5N1) virus in human serum by using a combination of serologic assays. J Clin Microbiol 37:937-43.
Rubinstein et al., 2000. Progressive specific immune attrition after primary, secondary and tertiary immunizations with bacteriophage phi X174 in asymptomatic HIV-1 infected patients. Aids 14:F55-62.
Saggio, I., and R. Laufer. 1993. Biotin binders selected from a random peptide library expressed on phage. Biochem J 293 ( Pt 3):613-6.
Sanger et al., 2001. Adverse effects of NVA-T7 on the transport of Marburg virus glycoprotein. Journal of Virological Methods. 91:29-35.
Santi et al., 2000. Bacteriophage lambda display of complex cDNA libraries: a new approach to functional genomics. J Mol Biol 296:497-508.
Saphire et al., 2001. Crystal structure of a neutralizing human IGG against HIV-1: a template for vaccine design. Science 293:1155-9.
Sathaliyawala et al., 2006. Assembly of human immunodeficiency virus (HIV) antigens on bacteriophage T4: a novel in vitro approach to construct multicomponent HIV vaccines. J Virol 80:7688-98.
Scott, J. K., and G. P. Smith. 1990. Searching for peptide ligands with an epitope library. Science 249:386-90.
Schoolnik et al., 2004. Phage offer a real alternative. Nat. Biotechnol. 5(22):505-6.
Sharp, P. M., and W. H. Li. 1987. The codon Adaptation Index—a measure of directional synonymous codon usage bias, and its potential applications. Nucleic Acids Res 15: 1281-95.
Siegrist et al., 2004. Co-administration of CpG oligonucleotides enhances the late affinity maturation process of human anti-hepatitis B vaccine response. Vaccine 23:615-22.
Silvera et al., 2002. Outcome of simian-human immunodeficiency virus strain 89.6p challenge following vaccination of rhesus macaques with human immunodeficiency virus Tat protein. J Virol 76:3800-9.
Silvera et al., 2004. Vaccination with gp120-depleted HIV-1 plus immunostimulatory CpG oligodeoxynucleotides in incomplete Freund's adjuvant stimulates cellular and humoral immunity in rhesus macaques. Vaccine 23:827-39.
Skrincosky et al., 2000. Identification and analysis of a novel heparin-binding glycoprotein encoded by human herpesvirus 7. J Virol 74:4530-40.
Slepushkin et al., 1995. Protection of mice against influenza A virus challenge by vaccination with baculovirus-expressed M2 protein. Vaccine 13:1399-402.
Smith, G. P. 1985. Filamentous fusion phage: novel expression vectors that display cloned antigens on the virion surface. Science 228:1315-7.
Solomon et al., 2005. Generation of anti-beta-amyloid antibodies via phage display technology towards Alzheimer's disease vaccination. Vaccine. 23:2327-2330.
Srivastava et al., 2002. Purification and characterization of oligomeric envelope glycoprotein from a primary R5 subtype B human immunodeficiency virus. J Virol 76:2835-47.
Srivastava, I. K., J. B. Ulmer, and S. W. Barnett. 2004. Neutralizing antibody responses to HIV: role in protective immunity and challenges for vaccine design. Expert Rev Vaccines 3:S33-52.
Stamatatos, L., M. Lim, and C. Cheng-Mayer. 2000. Generation and structural analysis of soluble oligomeric gp140 envelope proteins derived from neutralization-resistant and neutralization-susceptible primary HIV type 1 isolates. AIDS Res Hum Retroviruses 16:981-94.
Stephenson et al., 2004. Detection of anti-H5 responses in human sera by HI using horse erythrocytes following MF59-adjuvanted influenza AIDucMSingaporei97 vaccine. Virus Res 103:91-5.
Sternberg, N., and R. H. Hoess. 1995. Display of peptides and proteins on the surface of bacteriophage lambda. Proc Natl Acad Sci U S A 92:1609-13.
Sternberg, N., and R. Weisberg. 1977. Packaging of coliphage lambda DNA. II. The role of the gene D protein. J Mol Biol 117:733-59.
Stevens et al., 2006, Structure and receptor specificity of the hemagglutinin from an H5N1 influenza virus. Science 31 2:404-10.
Stevens et al., 2004. Structure of the uncleaved human HI hemagglutinin from the extinct 191 8 influenza virus. Science 303:1866-70.
Subbarao et al., 2003. Evaluation of a genetically modified reassortant H5N1 influenza A virus vaccine candidate generated by plasmid-based reverse genetics. Virology 305:192-200.
Sulakvelidze, A., Z. Alavidze, and J. G. Morris, Jr. 2001. Bacteriophage therapy. Antimicrob Agents Chemother 45:649-59.
Szathmary et al., 2004. Characterization of the DialGuard device for endotoxin removal in hemodialysis. Blood Purif 22:409-15.
Agadjanyan et al., 2005. Prototype Alzheimer's disease vaccine using the immunodominant B cell epitope from beta-amyloid and promiscuous T cell epitope pan HLA DR-binding peptide. J lmmunol 174:1580-6.
Alexander et al., 2000. Linear Padre T helper epitope and carbohydrate B cell epitope conjugates induce specific high titer IgG antibody responses. J lmmunol 164:1625-33.
Alexander et al., 1998. The optimization of helper T lymphocyte (HTL) function in vaccine development. lmmunol Res 18:79-92.
Alexander et al., 1994. Development of high potency universal DR-restricted helper epitopes by modification of high affinity DR-blocking peptides. Immunity 1:751-61.
Amoureux et al., 2004. A new method for removing endotoxin from plasma using hemocompatible affinity chromatography technology, applicable for extracorporeal treatment of septic patients. J Endotoxin Res 10:85-95.
Amoureux et al., 2004. Endotoxin removal from whole blood by a novel adsorption resin: efficiency and hemocompatibility. Int J Artif Organs 27:480-7.
Andre et al., 1998. Increased immune response elicited by DNA vaccination with a synthetic gp120 sequence with optimized codon usage. J Virol 72:1497-503.
Barbas et al., 1991. Assembly of combinatorial antibody libraries on phage surfaces: the gene III site. Proc Natl Acad Sci U S A 88:7978-82.
Barnett et al., 1997. Vaccination with HIV-1 gp120 DNA induces immune responses that are boosted by a recombinant gp120 protein subunit. Vaccine 15:869-73.
Barrow, P. A., and J. S. Soothill. 1997. Bacteriophage therapy and prophylaxis: rediscovery and renewed assessment of potential. Trends Microbiol 5:268-71.
Barrow et al., 1998. Use of lytic bacteriophage for control of experimental *Escherichia coli* septicemia and meningitis in chickens and calves. Clin. Diagn. Lab. Immunol. 5:294-8 (1998).
Bearden et al., 2005. Rituximab inhibits the in vivo primary and secondary antibody response to a neoantigen, bacteriophage phiX174. Am J Transplant 5:50-7.
Beigel et al., 2005. Avian influenza A (H5N1) infection in humans. N Engl J Med. 353:1374-85.
Benhar et al., 2001. Biotechnological applications of phage and cell display. Biotechnology Advances 19:1-33.
Bernasconi et al., 2003. A role for Toll-like receptors in acquired immunity: up-regulation of TLR9 by BCR triggering in naive B cells and constitutive expression in memory B cells. Blood 101:4500-4.
Bessette et al., 2004. Rapid isolation of high-affinity protein binding peptides using bacterial display. Protein Eng Des Sel 17:731-9.
Boland et al., 2004. Safety and immunogenicity profile of an experimental hepatitis B vaccine adjuvanted with AS04. Vaccine 23:316-20.
Bonnycastle et al., 1997. Assaying phage-borne peptides by phage capture on fibrinogen or streptavidin. Biol Chem 378:509-15.

(56) References Cited

OTHER PUBLICATIONS

Boratynski et al., 2004. Preparation of endotoxin-free bacteriophages. Cell Mol Biol Lett 9:253-9.
Bourke et al., 2003. The toll-like receptor repertoire of human B lymphocytes: inducible and selective expression of TLR9 and TLR10 in normal and transformed cells. Blood 102:956-63.
Bower et al., 2004. Elicitation of neutralizing antibodies with DNA vaccines expressing soluble stabilized human immunodeficiency virus type 1 envelope glycoprotein trimers conjugated to C3d. J Virol 78:4710-9.
Bradel-Tretheway et al., 2003. Effects of codon-optimization on protein expression by the human herpesvirus 6 and 7 U51 open reading frame. J Virol Methods 111:145-56.
Bresson et al., 2006. Safety and immunogenicity of an inactivated split-virion influenza ANietnam/1194/2004 (H5N1) vaccine: phase I randomized trial. Lancet 367(9523):1657-64 (2006).
Brett, I. C., and B. E. Johansson. 2005. Immunization against influenza A virus: comparison of conventional inactivated, live-attenuated and recombinant baculovirus produced purified hemagglutinin and neuraminidase vaccines in a murine model system. Virology 339:273-80.
Briggs et al., 2003. Structural organization of authentic, mature HIV-1 virions and cores. Embo J 22:1707-15.
Burton, D. R. 2006. Structural biology: images from the surface of HIV. Nature 441:817-8.
Burton et al., 2004. HIV vaccine design and the neutralizing antibody problem. Nat Immunol 5:233-6.
Calarese et al., 2005. Dissection of the carbohydrate specificity of the broadly neutralizing anti-HIV-1 antibody 2G12. Proc Natl Acad Sci U S A 102:13372-7.
Campos et al., 2004. Avidin-based targeting and purification of a protein IX-modified, metabolically biotinylated adenoviral vector. Mol Ther 9:942-54.
Caparon et al., 1996. Analysis of novel streptavidin-binding peptides, identified using a phage display library, shows that amino acids external to a perfectly conserved consensus sequence and to the presented peptides contribute to binding. Mol Divers 1:241-6.
Cid-Arregui, A., V. Juarez, and H. zur Hausen. 2003. A synthetic E7 gene of human papillomavirus type 16 that yields enhanced expression of the protein in mammalian cells and is useful for DNA immunization studies. J Virol 77:4928-37.
Chang et al., 2004. Crystal structure of a truncated version of the phage lambda protein gpD. Proteins 57:866-8.
Chauthaiwale et al., 1992. Bacteriophage lambda as a cloning vector. Microbiol. Mol. Biol. Rev. 56(4):577-591 (1992).
Chen et al., 2001. Protection of rhesus macaques against disease progression from pathogenic SHIV-89.6PD by vaccination with phage-displayed HIV-1 epitopes. Nat. Med. 7(11):1225-31.
Chen, B. Y., and H. C. Lim. 1996. Bioreactor studies on temperature induction of the Q-mutant of bacteriophage lambda in *Escherichia coli*. J Biotechnol 51:1-20.
Cherpelis et al., 2001. DNA vaccination with the human immunodeficiency virus type 1 SF162DeltaV2 envelope elicits immune responses that offer partial protection from simian/human immunodeficiency virus infection to CD8(+) T-cell-depleted rhesus macaques. J Virol 75:1547-50.
Clackson et al., 1991. Making antibody fragments using phage display libraries. Nature 352:624-8.
Cloutier et al., 2000. Streptabody, a high avidity molecule made by tetramerization of in vivo biotinylated, phage display-selected scFv fragments on streptavidin. Mol Immunol 37:1067-77.
Cooper et al., 2004. CPG 7909, an immunostimulatory TLR9 agonist oligodeoxynucleotide, as adjuvant to Engerix-B HBV vaccine in healthy adults: a double-blind phase I/II study. J Clin Immunol 24:693-701.
Crawford et al., 1999. Baculovirus-derived hemagglutinin vaccines protect against lethal influenza infections by avian H5 and H7 subtypes, Vaccine 17:2265-74.
De Berardinis et al., 1999. Recognition of HIV-derived B and T cell epitopes displayed on filamentous phages. Vaccine 17:1434-1441.
De Berardinis et al., 2000. Phage display of peptide epitopes from HIV-1 elicits strong cytolytic responses. Nat. Biotechnol. 18:873-876.
De Filette et al., 2005. Universal influenza A vaccine: optimization of M2-based constructs. Virology 337:149-61.
de Jong et al., 2005. Oseltamivir resistance during treatment of influenza A (H5N1) infection. N Engl J Med 353:2667-72.
de la Cruz et al., 1988. Immunogenicity and epitope mapping of foreign sequences via genetically engineered filamentous phage. J Biol Chem 263:4318-22.
del Guercio et al., 1997. Potent immunogenic short linear peptide constructs composed of B cell epitopes and Pan DR T helper epitopes (PADRE) for antibody responses in vivo. Vaccine 15:441-8.
Desombere et al., 2002. Immune response of HLA DQ2 positive subjects, vaccinated with HBsAg/AS04, a hepatitis B vaccine with a novel adjuvant. Vaccine 20:2597-602.
Devlin et al., 1990. Random peptide libraries: a source of specific protein binding molecules. Science 249:404-6.
Dokland, T., and H. Murialdo. 1993. Structural transitions during maturation of bacteriophage lambda capsids. J Mol Biol 233:682-94.
Dubos et al., 1943. The multiplication of bacteriophage in vivo and its protective effect against an experimental infection with *Shigella dysenteriae*. Journal Exp. Med. 78:161-168.
Earl et al., 2001. Immunogenicity and protective efficacy of oligomeric human immunodeficiency virus type 1 gp140. J Virol 75:645-53.
Eguchi et al., 2001. Protein transduction domain of HIV-1 Tat protein promotes efficient delivery of DNA into mammalian cells. J Biol Chem 276:26204-10.
Evans et al., 2001. A Phase 1 study of a recombinant viruslike particle vaccine against human papillomavirus type 11 in healthy adult volunteers. J Infect Dis 183:1485-93.
Feng et al., 2003. Design and assembly of anti-CD16 ScFv antibody with two different linker peptides. J Immunol Methods 282:33-43.
Fischer et al., 2003. Intranasal immunization of guinea pigs with an immunodominant foot-and-mouth disease virus peptide conjugate induces mucosal and humoral antibodies and protection against challenge. J Virol 77:7486-91.
Fogelman et al., 2000. Evaluation of CD4+ T cell function in vivo in HIV-infected patients as measured by bacteriophage phiX174 immunization. J Infect Dis 182:435-41.
Forrer, P., and R. Jaussi. 1998. High-level expression of soluble heterologous proteins in the cytoplasm of *Escherichia coli* by fusion to the bacteriophage lambda head protein D. Gene 224:45-52.
Frace et al., 1999. Modified M2 proteins produce heterotypic immunity against influenza A virus. Vaccine 17:2237-44.
Fukuma et al., 2005. True atomic resolution in liquid by frequency-modulation atomic force microscopy. Applied Physics Letters 87:034101.
Gantner et al., 2003. CD40-dependent and -independent activation of human tonsil B cells by CpG oligodeoxynucleotides. Eur J Immunol 33:1576-85.
Gerber et al., 2001. Human papillomavirus virus-like particles are efficient oral immunogens when coadministered with *Escherichia coli* heat-labile enterotoxin mutant R192G or CpG DNA. J Virol 75:4752-60.
Ghochikyan et al., 2005. Prototype Alzheimer's disease epitope vaccine induced strong Th2-type anti-Abeta antibody response with Alum to Quil A adjuvant switch. Vaccine 24(13):2275-2282 (2006).
Giannini et al., 2006. Enhanced humoral and memory B cellular immunity using HPV16/18 L1 VLP vaccine formulated with the MPL/aluminium salt combination (AS04) compared to aluminium salt only. Vaccine 24:5937-5949.
Gilbert et al., 2005. HIV-1 virologic and immunologic progression and initiation of antiretroviral therapy among HIV-1-infected subjects in a trial of the efficacy of recombinant glycoprotein 120 vaccine. J Infect Dis 192:974-83.
Gilbert et al., 2005. Correlation between immunologic responses to a recombinant glycoprotein 120 vaccine and incidence of HIV-1 infection in a phase 3 HIV-1 preventive vaccine trial. J Infect Dis 191:666-77.
Gorantla et al., 2005. Human dendritic cells transduced with herpes simplex virus amplicons encoding human immunodeficiency virus

(56) References Cited

OTHER PUBLICATIONS type 1 (HIV-1) gp120 elicit adaptive immune responses from human cells engrafted into NOD/SCID mice and confer partial protection against HIV-1 challenge. J Virol 79:2124-32.
Gorny et al., 2005. Identification of a new quaternary neutralizing epitope on human immunodeficiency virus type 1 virus particles. J Virol 79:5232-7.
Green et al., 2003. Enhancement of antibodies to the human immunodeficiency virus type 1 envelope by using the molecular adjuvant C3d. J Virol 77:2046-55.
Greenwood et al., 1991. Multiple display of foreign peptides on a filamentous bacteriophage. Peptides from *Plasmodium falciparum* circumsporozoite protein as antigens. J Mol Biol 220:821-7.
Grundner et al., 2005. Analysis of the neutralizing antibody response elicited in rabbits by repeated inoculation with trimeric HIV-1 envelope glycoproteins. Virology 331:33-46.
Grundner et al., 2004. Factors limiting the immunogenicity of HIV-1 gp120 envelope glycoproteins. Virology 330:233-48.
Guan et al., 2004. H5N1 influenza: a protean pandemic threat. Proc Natl Acad Sci U S A 101:8156-61.
Gupta et al., 2003. High-density functional display of proteins on bacteriophage lambda. J Mol Biol 334:241-54.
Haas, J., E. C. Park, and B. Seed. 1996. Codon usage limitation in the expression of HIV-1 envelope glycoprotein. Curr Biol 6:315-24.
Haigwood, N. L. 2004. Predictive value of primate models for AIDS. AIDS Rev 6:187-98.
Halstead, 2003. Neutralizataion and antibody-dependent enhancement of dengue viruses. Advances in Virus Research 60:421-467.
Hammonds et al., 2005. Induction of neutralizing antibodies against human immunodeficiency virus type 1 primary isolates by Gag-Env pseudovirion immunization. J Virol 79:14804-14.
Hanke et al., 1998. Enhancement of MHC class I-restricted peptide-specific T cell induction by a DNA prime/MVA boost vaccination regime. Vaccine 16:439-45.
Harper et al., 2004. Efficacy of a bivalent L1 virus-like particle vaccine in prevention of infection with human papillomavirus types 16 and 18 in young women: a randomised controlled trial. Lancet 364:1757-65.
Harper et al., 2006. Sustained efficacy up to 4.5 years of a bivalent L1 virus-like particle vaccine against human papillomavirus types 16 and 18: follow-up from a randomised control trial. Lancet 367:1247-55.
Herrera et al., 2005. The impact of envelope glycoprotein cleavage on the antigenicity, infectivity, and neutralization sensitivity of Env-pseudotyped human immunodeficiency virus type 1 particles. Virology 338:154-72.
Hershey, A. D., and W. Dove. 1983. Introduction to Lambda, p. 3-12. In R. W. Hendrix, J. W. Roberts, F. W. Stahl, and R. A. Weisberg (ed.), Lambda II. Cold Spring Harbor Press, New York.
Hirunpetcharat et al., 2003. CpG oligodeoxynucleotide enhances immunity against blood-stage malaria infection in mice parenterally immunized with a yeast-expressed 19 kDa carboxyl-terminal fragment of *Plasmodium yoelii* merozoite surface protein-1 (MSP1(19)) formulated in oil-based Montanides. Vaccine 21:2923-32.
Hocknell et al., 2002. Expression of human immunodeficiency virus type 1 gp120 from herpes simplex virus type 1-derived amplicons results in potent, specific, and durable cellular and humoral immune responses. J Virol 76:5565-80.
Hoess, R. H. 2002. Bacteriophage lambda as a vehicle for peptide and protein display. Curr Pharm Biotechnol 3:23-8.
Hogarth et al., 2003. Evaluation of adjuvants for protein vaccines against tuberculosis in guinea pigs. Vaccine 21:977-82.
Horimoto et al., 2004. Antigenic differences between H5N1 human influenza viruses isolated in 1997 and 2003. J Vet Med Sci 66:303-5.
Horimoto et al., 2006. The development and characterization of H5 influenza virus vaccines derived from a 2003 human isolate. Vaccine 24:3669-76.
Hornung et al., 2002. Quantitative expression of toll-like receptor 1-10 mRNA in cellular subsets of human peripheral blood mononuclear cells and sensitivity to CpG oligodeoxynucleotides. J Immunol 168:4531-7.
Lonescu et al., 2006. Pharmaceutical and immunological evaluation of human papillomavirus viruslike particle as an antigen carrier. J Pharm Sci 95:70-9.
Jepson, C. D., and J. B. March. 2004. Bacteriophage lambda is a highly stable DNA vaccine delivery vehicle. Vaccine 22:2413-9.
Kaiser, J. 2006. A one-size-fits-all flu vaccine? Science 312:380-2.
Katz, B. A. 1999. Streptavidin-binding and -dimerizing ligands discovered by phage display, topochemistry, and structure-based design. Biomol Eng 16:57-65.
Kretzschmar et al., 1995. Expression of the hemagglutinin protein of influenza virus. Analysis of protein modifications. Methods Mol Biol 39:317-36.
Kumar et al., 2004. CpG oligodeoxynucleotide and Montanide ISA 51 adjuvant combination enhanced the protective efficacy of a subunit malaria vaccine. Infect Immun 72:949-57.
Kuroda et al., 1986. Expression of the influenza virus haemagglutinin in insect cells by a baculovirus vector. Embo J 5:1359-65.
Kwong et al., 1998. Structure of an HIV gp120 envelope glycoprotein in complex with the CD4 receptor and a neutralizing human antibody. Nature 393:648-59.
Lakey et al., 1996. Recombinant baculovirus influenza A hemagglutinin vaccines are well tolerated and immunogenic in healthy adults. J Infect Dis 174:838-41.
Larocca et al., 1998. Targeting bacteriophage to mammalian cell surface receptors for gene delivery. Hum Gene Ther 9:2393-9.
Lawrence et al., 1998. Orientation of antigen binding sites in dimeric and trimeric single chain Fv antibody fragments. FEBS Lett 425:479-84.
Le Gall et al., 2004. Effect of linker sequences between the antibody variable domains on the formation, stability and biological activity of a bispecific tandem diabody. Protein Eng Des Sel 17:357-66.
Lesley, S. A., and D. J. Groskreutz. 1997. Simple affinity purification of antibodies using in vivo biotinylation of a fusion protein. J Immunol Methods 207:147-55.
Letvin et al., 1997. Potent, protective anti-HIV immune responses generated by bimodal HIV envelope DNA plus protein vaccination. Proc Natl Acad Sci U S A 94:9378-83.
Levie et al., 2002. A 2-dose regimen of a recombinant hepatitis B vaccine with the immune stimulant AS04 compared with the standard 3-dose regimen of Engerix-B in healthy young adults. Scand J Infect Dis 34:610-4.
Li, et al., 2005 Chimeric influenza virus hemagglutinin proteins containing large domains of the *Bacillus anthracis* protective antigen: protein characterization, incorporation into infectious influenza viruses, and antigenicity. J Virol 79:10003-12.
Li, et al., 2004. Genesis of a highly pathogenic and potentially pandemic H5N1 influenza virus in eastern Asia. Nature 430:209-13.
Li et al., 2006. Characterization of antibody responses elicited by human immunodeficiency virus type 1 primary isolate trimeric and monomeric envelope glycoproteins in selected adjuvants. J Virol 80:1414-26.
Li et al., 2006. Bacteriophage T4 capsid: a unique platform for efficient surface assembly of macromolecular complexes Journal of Molecular Biology 363(2):577-588.
Lipatov et al., 2005. Efficacy of H5 influenza vaccines produced by reverse genetics in a lethal mouse model. J Infect Dis 191:1216-20.
Maines et al., 2005. Avian Influenza (H5N1) Viruses Isolated from Humans in Asia in 2004 Exhibit Increased Virulence in Mammals. J Virol 79:11788-800.
Maguire et al., 2006. Recombinant adenovirus type 5 vectors that target DC-SIGN, ChemR23 and alpha(v)beta3 integrin efficiently transduce human dendritic cells and enhance presentation of vectored antigens. Vaccine 24:671-82.
Marciani et al., 2000. Development of semisynthetic triterpenoid saponin derivatives with immune stimulating activity. Vaccine 18:3141-51.
Marciani et al., 2003. Fractionation, structural studies, and immunological characterization of the semi-synthetic *Quillaja saponins* derivative GPI-0100. Vaccine 21:3961-71.

(56) References Cited

OTHER PUBLICATIONS

Maruyama et al., 1994. Lambda foo: a lambda phage vector for the expression of foreign proteins. Proc Natl Acad Sci U S A 91:8273-7.

Mascola, J. R. 2003. Defining the protective antibody response for HIV-1. Curr Mol Med 3:209-16.

Mascola et al., 2005. Recommendations for the design and use of standard virus panels to assess neutralizing antibody responses elicited by candidate human immunodeficiency virus type 1 vaccines. J Virol 79:10103-7.

Mase et al., 2005. Characterization of H5N1 influenza A viruses isolated during the 2003-2004 influenza outbreaks in Japan. Virology 332:167-76.

* cited by examiner gpD 3JCLI4 DUAL CDF3JCLI4 DUAL

Dec. (gpD+) Undec. (gpD-) MWM

- 20 kD

SEQUENCE LISTING

```
<160> NUMBER OF SEQ ID NOS: 34

<210> SEQ ID NO 1
<211> LENGTH: 110
<212> TYPE: PRT
<213> ORGANISM: Enterobacteria phage lambda

<400> SEQUENCE: 1

Met Thr Ser Lys Glu Thr Phe Thr His Tyr Gln Pro Gln Gly Asn Ser
 1               5                  10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val
            100                 105                 110


<210> SEQ ID NO 2
<211> LENGTH: 246
<212> TYPE: PRT
<213> ORGANISM: Enterobacteria phage lambda

<400> SEQUENCE: 2

Met Pro Val Pro Asn Pro Thr Met Pro Val Lys Gly Ala Gly Thr Thr
 1               5                  10                  15

Leu Trp Val Tyr Lys Gly Ser Gly Asp Pro Tyr Ala Asn Pro Leu Ser
            20                  25                  30

Asp Val Asp Trp Ser Arg Leu Ala Lys Val Lys Asp Leu Thr Pro Gly
        35                  40                  45

Glu Leu Thr Ala Glu Ser Tyr Asp Asp Ser Tyr Leu Asp Asp Glu Asp
    50                  55                  60

Ala Asp Trp Thr Ala Thr Gly Gln Gly Gln Lys Ser Ala Gly Asp Thr
65                  70                  75                  80

Ser Phe Thr Leu Ala Trp Met Pro Gly Glu Gln Gly Gln Gln Ala Leu
```

```
                85                  90                  95

Leu Ala Trp Phe Asn Glu Gly Asp Thr Arg Ala Tyr Lys Ile Arg Phe
            100                 105                 110

Pro Asn Gly Thr Val Asp Val Phe Arg Gly Trp Val Ser Ser Ile Gly
        115                 120                 125

Lys Ala Val Thr Ala Lys Glu Val Ile Thr Arg Thr Val Lys Val Thr
    130                 135                 140

Asn Val Gly Arg Pro Ser Met Ala Glu Asp Arg Ser Thr Val Thr Ala
145                 150                 155                 160

Ala Thr Gly Met Thr Val Thr Pro Ala Ser Thr Ser Val Val Lys Gly
                165                 170                 175

Gln Ser Thr Thr Leu Thr Val Ala Phe Gln Pro Glu Gly Val Thr Asp
            180                 185                 190

Lys Ser Phe Arg Ala Val Ser Ala Asp Lys Thr Lys Ala Thr Val Ser
        195                 200                 205

Val Ser Gly Met Thr Ile Thr Val Asn Gly Val Ala Ala Gly Lys Val
    210                 215                 220

Asn Ile Pro Val Val Ser Gly Asn Gly Glu Phe Ala Ala Val Ala Glu
225                 230                 235                 240

Ile Thr Val Thr Ala Ser
                245


<210> SEQ ID NO 3
<211> LENGTH: 741
<212> TYPE: DNA
<213> ORGANISM: Enterobacteria phage lambda

<400> SEQUENCE: 3

atgcctgtac caaatcctac aatgccggtg aaaggtgccg ggaccaccct gtgggtttat      60

aaggggagcg gtgaccctta cgcgaatccg ctttcagacg ttgactggtc gcgtctggca     120

aaagttaaag acctgacgcc cggcgaactg accgctgagt cctatgacga cagctatctc     180

gatgatgaag atgcagactg gactgcgacc gggcaggggc agaaatctgc cggagatacc     240

agcttcacgc tggcgtggat gcccggagag caggggcagc aggcgctgct ggcgtggttt     300

aatgaaggcg atacccgtgc ctataaaatc cgcttcccga acggcacggt cgatgtgttc     360

cgtggctggg tcagcagtat cggtaaggcg gtgacggcga aggaagtgat cacccgcacg     420

gtgaaagtca ccaatgtggg acgtccgtcg atggcagaag atcgcagcac ggtaacagcg     480

gcaaccggca tgaccgtgac gcctgccagc acctcggtgg tgaaagggca gagcaccacg     540

ctgaccgtgg ccttccagcc ggagggcgta accgacaaga gctttcgtgc ggtgtctgcg     600

gataaaacaa aagccaccgt gtcggtcagt ggtatgacca tcaccgtgaa cggcgttgct     660

gcaggcaagg tcaacattcc ggttgtatcc ggtaatggtg agtttgctgc ggttgcagaa     720

attaccgtca ccgccagtta a                                               741


<210> SEQ ID NO 4
<211> LENGTH: 468
<212> TYPE: DNA
<213> ORGANISM: Artificial Sequence
<220> FEATURE:
<223> OTHER INFORMATION: Synthetically generated oligonucleotide

<400> SEQUENCE: 4

cgactcacta tagggcgaat tgggtaccgg gcccccctc gagcgaggta ccatatggga       60

attcgaagct ttcatgacca gcaaggaaac atttacgcat taccagccgc aagggaactc     120
```

```
tgatcccgcg cacaccgcca ccgccccggg cggactgtca gcgaaggccc cggccatgac    180

tcctctgatg ttagatacga gcagtcggaa acttgtggcg tgggacggta ctaccgatgg    240

tgcagcggtc ggcattttgg cagttgcagc tgaccagaca tcgaccactc tgacattcta    300

taaatccggc acctttcgtt atgaggatgt gctctggcca gaagccgctt ctgacgaaac    360

gaaaaaacgc acggcgttcg cgggcaccgc aatcagtatt gtaggatctg gtggcggttc    420

cggcggtgga tccgtcgacg atatcgaccg agctccagct tttgttcc                 468
```

<210> SEQ ID NO 5
<211> LENGTH: 741
<212> TYPE: DNA
<213> ORGANISM: Enterobacteria phage lambda

<400> SEQUENCE: 5

```
atgcctgtac caaatcctac aatgccggtg aaaggtgccg ggaccaccct gtgggtttat     60

aaggggagcg gtgaccctta cgcgaatccg ctttcagacg ttgactggtc gcgtctggca    120

aaagttaaag acctgacgcc cggcgaactg accgctgagt cctatgacga cagctatctc    180

gatgatgaag atgcagactg gactgcgacc gggcaggggc agaaatctgc cggagatacc    240

agcttcacgc tggcgtggat gcccggagag caggggcagc aggcgctgct ggcgtggttt    300

aatgaaggcg atacccgtgc ctataaaatc cgcttcccga acggcacggt cgatgtgttc    360

cgtggctggg tcagcagtat cggtaaggcg gtgacggcga aggaagtgat cacccgcacg    420

gtgaaagtca ccaatgtggg acgtccgtcg atggcagaag atcgcagcac ggtaacagcg    480

gcaaccggca tgaccgtgac gcctgccagc acctcggtgg tgaaagggca gagcaccacg    540

ctgaccgtgg ccttccagcc ggagggcgta accgacaaga gctttcgtgc ggtgtctgcg    600

gataaaacaa aagccaccgt gtcggtcagt ggtatgacca tcaccgtgaa cggcgttgct    660

gcaggcaagg tcaacattcc ggttgtatcc ggtaatggtg agtttgctgc ggttgcagaa    720

attaccgtca ccgccagtta a                                              741
```

<210> SEQ ID NO 6
<211> LENGTH: 115
<212> TYPE: PRT
<213> ORGANISM: Enterobacteria phage lambda

<400> SEQUENCE: 6

```
Met Val Thr Lys Thr Ile Thr Glu Gln Arg Ala Glu Val Arg Ile Phe
 1               5                  10                  15

Ala Gly Asn Asp Pro Ala His Thr Ala Thr Gly Ser Ser Gly Ile Ser
            20                  25                  30

Ser Pro Thr Pro Ala Leu Thr Pro Leu Met Leu Asp Glu Ala Thr Gly
        35                  40                  45

Lys Leu Val Val Trp Asp Gly Gln Lys Ala Gly Ser Ala Val Gly Ile
    50                  55                  60

Leu Val Leu Pro Leu Glu Gly Thr Glu Thr Ala Leu Thr Tyr Tyr Lys
65                  70                  75                  80

Ser Gly Thr Phe Ala Thr Glu Ala Ile His Trp Pro Glu Ser Val Asp
                85                  90                  95

Glu His Lys Lys Ala Asn Ala Phe Ala Gly Ser Ala Leu Ser His Ala
            100                 105                 110

Ala Leu Pro
        115
```

<210> SEQ ID NO 7

<211> LENGTH: 8134
<212> TYPE: DNA
<213> ORGANISM: Enterobacteria phage lambda

<400> SEQUENCE: 7

```
aatatttctg attttcattt gatgatgcct ctgtgtgaaa tgacggtaaa cgacgcactt     60
gtgccggcac ataatagcaa gcaccataat agatcagatt cgattcttgc tgtaagtgat    120
aattattctc gttttcgggt cctttccgtc gatccaacag gttacggggc ggcgacctcg    180
cggtttttca ctatttatga aatttttca gggaaaatcg tgtcggtact tctcgaatat    240
aactttttgt ttttttaat attgcatccg taaaggtccg acatgaaagt gtccgaaaat    300
gccttttct ggcgttttca tgtcgggcct tgtatttgat aatgggttgt tttcatgaag    360
gttaataaaa agaggcttgc cgaaattttc aacgtggacc cgcggacgat tgaacgctgg    420
cagtctcagg gactcccttg cgcctccaaa ggtagtaagg gcattgaatc tgtatttgat    480
actgccatgg caattcagtg gtatgcgcag agggaaactg atatcgaaaa cgaaaagctc    540
cgcaaagaac tggacgattt gcgtgcggca gcggagtcag atttacaacc cggcaccatt    600
gactatgaac gctaccggct cacaaaagcg caggcagatg cgcaggaact gaaaaatgcc    660
cgtgaagacg gagtagtgct ggaaactgaa ctgtttacct tcattctgca acgtgtggca    720
caggagattt cggggatact tgtgcgtgtg ccgttgacat tacagcgtaa atatccggac    780
atttcaccat cacaccttga tgtggtgaaa actgaaatcg cgaaagcctc caatgttgca    840
gctaaggccg gtgaaaacgt gggcgggtgg atcgatgatt tcagacgcgc agaaggcagc    900
taatgcagcc ggtgcgatag ctacagggct tttatctctc attattcctg ttccactgac    960
gacagttcag tgggccaata aacattatta ccttcctaaa gagtcgtctt ataccccggg   1020
gcgatgggaa acactgccgt ttcaggttgg catcatgaac tgtatgggca acgatctgat   1080
tcgcacggtt aacctgatta aatctgcccg tgttggttat acaaagatgt tgctgggagt   1140
ggaggcttat tttattgagc ataaatcacg caacagcctt ctttttcagc ccacggactc   1200
agctgctgaa gattttatga aatctcatgt tgagccaacg ataagggatg ttcctgctat   1260
gctggagctg gctccatggt tcggaagaaa acaccgcgat aatacgctca ccctgaagcg   1320
tttttcctcc ggtgtggggt tctggtgtct gggtggtgcg gcagcaaaaa actaccgtga   1380
aaaatccgtg gatgtggtct gttatgacga gctttcctcg ttcgaaccgg atgttgaaaa   1440
agagggttcg ccaaccctgc tggggggataa acgtattgag ggctctgtat ggccaaaatc   1500
cattcgcggc tcgacgccaa aaatcaaagg ctcctgccag atcgaaaaag ccgctaacga   1560
gtcggcacac ttcatgcgtt tttatgtgcc ctgtccgcac tgtggggagg agcagtatct   1620
gaaatttggc gatgatgcct cgcctttcgg tcttaagtgg gagaagaata agccagaaag   1680
tgttttctac ctttgcgagc atcatggctg tgtgatccat cagtctgagc ttgaccagag   1740
taacgggcgg tggatctgtg aaaacacggg catgtggacc cgtgacggcc tgatgttttt   1800
cagcgcccgg ggtgatgaaa ttccgccgcc gcgctccatc actttccata tctggacggc   1860
gtacagtccg ttcaccacct gggtacagat tgtctatgac tggctggatg cactgaaaga   1920
tcccaacggc ctgaaaacct ttgtgaacac cacgctgggc gagacctggg aagaggctgt   1980
gggcgaaaaa ctcgatcacc aggtgctgat ggataaggtt gtgcgttaca cggcggcggt   2040
gcctgcccgg gtggtttatc tgacggcggg cattgactcg cagcgaaacc gttttgagat   2100
gtatgtctgg ggatgggctc cgggagagga agcctttctg gtggataaaa tcatcattat   2160
ggggcgtccc gatgaggaag agacgctgtt acgtgtggat gcggcgatca acaaaaaata   2220
```

-continued

```
ccgccatgca gacggaaccg aaatgaccat ttcccgtgtc tgctgggaca tcggggggat   2280

cgatggcgaa atcgtttatc agaggtcaaa aaaacacggt gttttccggg tgctgccggt   2340

aaaaggcgca tctgtctatg gcaagccggt gatcaccatg ccaaaaaccc gcaatcagcg   2400

gggcgtgtat ctgtgtgaag tggggacgga caccgcaaaa gaaattctct atgcccgtat   2460

gaaagccgat cccacgcctg tggatgaagc cacgtcgtat gctatccgtt ttcctgatga   2520

tccggagatt ttttcgcaga cagaggcgca gcaactggtc gcggaagagc ttgtggagaa   2580

gtgggaaaaa ggaaagatgc gtctgctgtg ggataacaaa aagcggcgta acgaagcgct   2640

ggactgcctg gtgtatgcct acgcggcatt acgtgtgtcc gtgcaacgct ggcagcttga   2700

tctggctgta ctggcaaaat cccgggaaga agagacgacc cggccaaccc ttaaagaact   2760

ggcagcgaag ctgtccggag gagtgaatgg ttacagtcgc tgaactgcag gcgctgcgtc   2820

aggcgcgcct tgatttatta accggtaaac gggtggtgtc tgtccagaaa gatggtcgca   2880

gaattgaata tacggcggct tctctggatg agcttaaccg ggcgatcaat gatgcggagt   2940

cggtactggg gacaacccgg tgtcgccgtc gtccgctggg agtgaggtta tgaaacgaac   3000

gcctgtcctg attgatgtga acggcgttcc gcttcgtgag agtctcagct acaacggggg   3060

cggtgcagga tttggcgggc aaatggctga gtggttgcca ccggcgcaga gtgccgatgc   3120

ggccctgctg cccgcgttgc gtctggggaa tgcccgggca gatgatctgg tgcgcaataa   3180

cggaatagcg gctaatgcgg tggctctgca taaggatcac attgtcgggc atatgtttct   3240

gatcagctac cgtccgaact ggcgctggct ggggatgcgg gagaccgcag caaaaagctt   3300

tgtcgatgag gtggaggcgg cctggtcgga atacgccgaa gggatgtttg gcgagatcga   3360

cgtggaagga aaacgcacgt tcacggaatt tatccgtgaa ggtgtgggcg ttcatgcgtt   3420

taacggcgaa atctttgtgc agccggtctg ggatacggaa accacgcagt tattccgtac   3480

gcgttttaaa gccgtgagtc cgaaacgggt ggacacgcct ggacacggta tggggaaccg   3540

ttttctgcgg gccggtgtgg aggtcgatcg atatggccgt gccgtcgcgt accatatctg   3600

tgaggatgat tttccgttct ctggtagtgg acgatgggaa cggatcccgc gtgaacttcc   3660

caccgggcgt ccggccatgc tgcatatttt cgagccggtg gaggacgggc agacccgtgg   3720

ggctaatcag ttttacagcg tcatggaacg gctgaagatg ctcgattccc tgcaggcaac   3780

acagcttcag tcggccatag tgaaggcgat gtatgcagcg acgattgaaa gtgaacttga   3840

taccgaaaag gcctttgaat atatcgccgg cgcgccacag gagcagaagg ataatccgct   3900

tattaatatt ctggagaagt tttccagctg gtatgacacg aataacgtga cactgggcgg   3960

tgtcaaaatt ccgcaccttt tccctggtga tgatctgaaa ctacagactg cgcaggattc   4020

agacaatgga ttttctgcgc ttgaacaggc gctgctgcgg tatatcgccg ccggtcttgg   4080

cgtttcctac gaacagttgt cccgtgatta ctcgaaggtc agttactcaa gtgcccgcgc   4140

ctccgccaat gagtcgtggc gctattttat ggggcggcga aaatttattg cggcccggct   4200

ggccacgcag atgttttcct gctggctgga agaggcactt cttcgggggga ttattcgtcc   4260

gccacgggca cgttttgatt tttatcaggc gcgatcagcc tggtcacggg cagagtggat   4320

tggtgccgga agaatggcca ttgacgggct caaggaagtc caggaatcag tgatgcgcat   4380

tgaggccgga ctgagcacgt atgagaaagg gctggcgctg atgggcgagg attatcagga   4440

cattttccgc cagcaggtca gggaatctgc tgagcggcaa aaagccggac tctcacgtcc   4500

ggtgtggata gagcaggcgt atcagcagca gatagcggag agtcgtaggc cggaagagga   4560

gacaacacca cgtgagacgt aatctttcac acattattgc cgcagcattc aatgaaccgc   4620
```

```
tgcttctgga gcccgcctat gcgcgggttt tcttttgcgc gctcgggcgc gagatggggg   4680
cagcaagtct ttcggtacca caacagcagg tacagtttga tgctcccgga atgctggctg   4740
aaacggacga gtacatggcc ggaggtaaac gaccggcccg tgtttaccgg gtggtgaacg   4800
gtattgctgt actgccggtg accggcacgc tggtgcaccg gctgggtggt atgcggccat   4860
tttccggaat gacaggctat gacggcattg tcgcctgtct tcagcaggca atggcggata   4920
gccaggtgcg gggcgtactg ctggacattg acagtccggg cgggcaggcc gccggcgcgt   4980
ttgactgcgc tgacatgatt taccgcctcc gtcagcagaa gccggtctgg gcactgtgca   5040
atgacacggc ctgttctgca gccatgctgc tggcgtcggc ctgctcccga cggctggtta   5100
cccagacatc ccgtatcggc tccattggcg tgatgatgag ccatgtcagc tatgccggtc   5160
atctggcgca ggccggtgtg gatatcacgc tgatttactc aggggcgcac aaggtggatg   5220
gcaatcagtt tgaagcgttg ccggcagagg ttcgccagga catgcagcag cggattgatg   5280
cggcgcgccg gatgtttgcc gaaaaagtgg cgatgtatac cggtctgtct gttgatgccg   5340
tcacgggaac agaggctgcc gtttttgaag gtcagtccgg cattgaggcc gggctggcgg   5400
atgaattaat caatgcgtcg gatgccatca gtgtgatggc cacggcgctg aacagtaatg   5460
tcagaggagg cactatgccg caattaactg caacggaagc cgccgcgcag gagaaccagc   5520
gagtgatggg gatcctgaca tgccaggaag cgaaaggacg tgaacagctt gccacgatgc   5580
tggcaggaca acagggcatg agcgttgaac aggcccgggc gattctggcc gcggcggcac   5640
cgcagcagcc ggtggcatcc acgcagagtg aagccgatcg cattatggtg tgtgaagaag   5700
cgaacggtcg tgaacaactg gcggcaacgc tggcggcgat gccggagatg acggtggaaa   5760
aagcccgccc gatcctggct gcttcaccgc aggcggatgc cggaccatca ctccgtgatc   5820
agatcatggc actggatgag gcaaaagggg ctgaggcgca ggctgaacag ctggctgcct   5880
gcccgggaat gacagtggag agcgcccggg ctgtgctggc tgcgggatca ggtaaggcag   5940
aaccggtctc tgcatccaca accgccatgt ttgaacattt catggcgaac cattcaccgg   6000
cagcggtaca gggtggcgtg gcacagacgt cagcagacgg tgatgcggac gtgaaaatgc   6060
tcatggccat gccatgaagt cagtgctgac catcaatagg aggtttttac aatatggtga   6120
cgaaaaccat cactgaacag cgtgcggaag tacgtatttt tgccggtaat gatccggctc   6180
ataccgccac aggcagcagc gggatttcct cgccaacacc ggcactgacg cccctgatgc   6240
tggatgaagc caccgggaaa ctggtggtct gggacggaca gaaagccggt agtgcggttg   6300
gcatactggt actgccgctt gaaggcacag agacggcgct gacgtattac aagtcgggaa   6360
cctttgcgac ggaggcaatc cactggcctg aaagtgtgga tgaacacaaa aaggccaacg   6420
cctttgctgg cagtgccctg agtcacgcgg cgctgccgta acacgttatc aggccaccgc   6480
ggtggcctga ctgatttctg aatgaaagga actgatttat gggattgttt acgacccgcc   6540
agttactcgg ttataccgaa caaaaagtta aatttcgtgc gctgtttctg gagctgtttt   6600
tccgccgtac ggtgaatttc cataccgaag aggtgatgct ggacaaaatt accggaaaaa   6660
cgccggtggc ggcctatgtc tccccggttg ttgaaggaaa agtgctgcgt catcgtggtg   6720
gtgaaacccg cgtgttgcgt ccgggctacg tcaagccgaa acacgaattt aattaccagc   6780
aggcggttga gcgccttcct ggtgaagatc catctcaact gaatgatccg gcttaccgcc   6840
gtctgcgtat cattaccgat aacctcaaac aggaagagca cgcgattgtc caggtggaag   6900
aaatgcaggc ggtaaatgct gtgttgtatg gcaaatacac catggaagga gaccagttcg   6960
agaaaattga ggtcgatttt ggcaggtcga cgaagaataa catcactcag ggtagtggta   7020
```

```
aggagtggtc aaaacaggat cgtgacacgt tcgatcctac acatgatatt gacctctact   7080

gcgacctggc cagcggtctt gtgaatattg ccattatgga cggtaccgtc tggcgtcttc   7140

tgaatggttt taagctgttc cgcgaaaaac tggataccgg tcgcggttca aattctcaac   7200

tcgaaacggc agtgaaagat ctgggcgcag tggtgtcctt caaggggtat tacggcgatc   7260

tggccattgt ggtggcgaaa acgtcttata tagcagaaga cggtatcgaa aaacgttatc   7320

ttccagatgg catgctggtt ctggggaata ctgctgcaga tgggatccgt tgttacggtg   7380

ccattcagga tgctcaggcg ttgtccgaag gtgtggtggc ctcttcccgt tatccgaaac   7440

actggctgac ggtaggggat cccgcccgtg aatttaccat gacgcagtcc gcgccgctga   7500

tggtgttgcc ggacccggat gagtttgtgg tggtacaggt gaaataatcc gtgagcgggg   7560

gcgaaatgcc cccgtgtctt ttttcacagg gggctgatat ggcaacgaaa gagcaaaatc   7620

tgaaacggct tgatgaactg gccctgattc tggggcgtga gccggatata tccgggagtg   7680

ccgcagagat agcgcagcgg gtggcagaat gggaagagga aatgcagtca tccggcgatg   7740

atgtacaggt tatgaatatg gatatccggg agcgggaaac cgcggctcat gatgttcgtg   7800

aggaaacatc cggcgcgtta acgcgcatca gagttctgac ctgcctccat ctctgtggcg   7860

ttgatggtga aacgggggaa tccgttgagc ttgcggatgt tggtcgggtg attctgatta   7920

tgtcctcaga tgcaaaaaca cacgttgatg gtggaatggc tgtttatgcg tgattttcag   7980

aatgcctttg atgccgccct tgccggggtg gacagtacga ttgttgaagt gatgggcatc   8040

agtgcgcagt tcacctccgg tgcacagcgt ggcggcgagg ttcatggcgt ttttgacgat   8100

ccggagtcgc tgggttttgc cagtagtggg atcc                               8134
```

<210> SEQ ID NO 8
<211> LENGTH: 341
<212> TYPE: PRT
<213> ORGANISM: Enterobacteria phage lambda

<400> SEQUENCE: 8

```
Met Ser Met Tyr Thr Thr Ala Gln Leu Leu Ala Ala Asn Glu Gln Lys
1               5                   10                  15

Phe Lys Phe Asp Pro Leu Phe Leu Arg Leu Phe Phe Arg Glu Ser Tyr
            20                  25                  30

Pro Phe Thr Thr Glu Lys Val Tyr Leu Ser Gln Ile Pro Gly Leu Val
        35                  40                  45

Asn Met Ala Leu Tyr Val Ser Pro Ile Val Ser Gly Glu Val Ile Arg
    50                  55                  60

Ser Arg Gly Gly Ser Thr Ser Glu Phe Thr Pro Gly Tyr Val Lys Pro
65                  70                  75                  80

Lys His Glu Val Asn Pro Gln Met Thr Leu Arg Arg Leu Pro Asp Glu
                85                  90                  95

Asp Pro Gln Asn Leu Ala Asp Pro Ala Tyr Arg Arg Arg Arg Ile Ile
            100                 105                 110

Met Gln Asn Met Arg Asp Glu Glu Leu Ala Ile Ala Gln Val Glu Glu
        115                 120                 125

Met Gln Ala Val Ser Ala Val Leu Lys Gly Lys Tyr Thr Met Thr Gly
    130                 135                 140

Glu Ala Phe Asp Pro Val Glu Val Asp Met Gly Arg Ser Glu Glu Asn
145                 150                 155                 160

Asn Ile Thr Gln Ser Gly Gly Thr Glu Trp Ser Lys Arg Asp Lys Ser
                165                 170                 175

Thr Tyr Asp Pro Thr Asp Asp Ile Glu Ala Tyr Ala Leu Asn Ala Ser
```

```
            180                 185                 190

Gly Val Val Asn Ile Ile Val Phe Asp Pro Lys Gly Trp Ala Leu Phe
        195                 200                 205

Arg Ser Phe Lys Ala Val Lys Glu Lys Leu Asp Thr Arg Arg Gly Ser
    210                 215                 220

Asn Ser Glu Leu Glu Thr Ala Val Lys Asp Leu Gly Lys Ala Val Ser
225                 230                 235                 240

Tyr Lys Gly Met Tyr Gly Asp Val Ala Ile Val Val Tyr Ser Gly Gln
                245                 250                 255

Tyr Val Glu Asn Gly Val Lys Lys Asn Phe Leu Pro Asp Asn Thr Met
            260                 265                 270

Val Leu Gly Asn Thr Gln Ala Arg Gly Leu Arg Thr Tyr Gly Cys Ile
        275                 280                 285

Gln Asp Ala Asp Ala Gln Arg Glu Gly Ile Asn Ala Ser Ala Arg Tyr
    290                 295                 300

Pro Lys Asn Trp Val Thr Thr Gly Asp Pro Ala Arg Glu Phe Thr Met
305                 310                 315                 320

Ile Gln Ser Ala Pro Leu Met Leu Leu Ala Asp Pro Asp Glu Phe Val
                325                 330                 335

Ser Val Gln Leu Ala
            340


<210> SEQ ID NO 9
<211> LENGTH: 341
<212> TYPE: PRT
<213> ORGANISM: Artificial Sequence
<220> FEATURE:
<223> OTHER INFORMATION: Mutant of Enterobacteria phage lambda

<400> SEQUENCE: 9

Met Ser Met Tyr Thr Thr Ala Gln Leu Leu Ala Ala Asn Glu Gln Lys
 1               5                  10                  15

Phe Lys Phe Asp Pro Leu Phe Leu Arg Leu Phe Phe Arg Glu Ser Tyr
            20                  25                  30

Pro Phe Thr Thr Glu Lys Val Tyr Leu Ser Gln Ile Pro Gly Leu Val
        35                  40                  45

Asn Met Ala Leu Tyr Val Ser Pro Ile Val Ser Gly Glu Val Ile Arg
    50                  55                  60

Ser Arg Gly Gly Ser Thr Ser Glu Phe Thr Pro Gly Tyr Val Lys Pro
65                  70                  75                  80

Lys His Glu Val Asn Pro Gln Met Thr Leu Arg Arg Leu Pro Asp Glu
                85                  90                  95

Asp Pro Gln Asn Leu Ala Asp Pro Ala Tyr Arg Arg Arg Arg Ile Ile
            100                 105                 110

Met Gln Asn Met Arg Asp Glu Glu Leu Ala Ile Ala Gln Val Glu Glu
        115                 120                 125

Met Gln Ala Val Ser Ala Val Leu Lys Gly Lys Tyr Thr Met Thr Gly
    130                 135                 140

Glu Ala Phe Asp Pro Val Glu Val Asp Met Gly Arg Ser Glu Glu Asn
145                 150                 155                 160

Asn Ile Thr Gln Ser Gly Gly Thr Lys Trp Ser Lys Arg Asp Lys Ser
                165                 170                 175

Thr Tyr Asp Pro Thr Asp Asp Ile Glu Ala Tyr Ala Leu Asn Ala Ser
            180                 185                 190

Gly Val Val Asn Ile Ile Val Phe Asp Pro Lys Gly Trp Ala Leu Phe
        195                 200                 205
```

```
Arg Ser Phe Lys Ala Val Lys Glu Lys Leu Asp Thr Arg Arg Gly Ser
    210                 215                 220

Asn Ser Glu Leu Glu Thr Ala Val Lys Asp Leu Gly Lys Ala Val Ser
225                 230                 235                 240

Tyr Lys Gly Met Tyr Gly Asp Val Ala Ile Val Val Tyr Ser Gly Gln
                245                 250                 255

Tyr Val Glu Asn Gly Val Lys Lys Asn Phe Leu Pro Asp Asn Thr Met
            260                 265                 270

Val Leu Gly Asn Thr Gln Ala Arg Gly Leu Arg Thr Tyr Gly Cys Ile
        275                 280                 285

Gln Asp Ala Asp Ala Gln Arg Glu Gly Ile Asn Ala Ser Ala Arg Tyr
    290                 295                 300

Pro Lys Asn Trp Val Thr Thr Gly Asp Pro Ala Arg Glu Phe Thr Met
305                 310                 315                 320

Ile Gln Ser Ala Pro Leu Met Leu Leu Ala Asp Pro Asp Glu Phe Val
                325                 330                 335

Ser Val Gln Leu Ala
            340


<210> SEQ ID NO 10
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 10

Gly Gly Gly Gly Ser Gly Gly Gly Gly Ser Gly Gly Gly Gly Ser
 1               5                  10                  15


<210> SEQ ID NO 11
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 11

Gly Ser Gly Ser Gly Ser
 1               5


<210> SEQ ID NO 12
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 12

Gly Ser Gly Gly Gly Ser Gly Gly Gly Ser Gly Gly Thr
 1               5                  10


<210> SEQ ID NO 13
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 13

Ser Ala Lys Thr Thr Pro
 1               5
```

<210> SEQ ID NO 14
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 14

Arg Ala Asp Ala Ala Pro
1 5

<210> SEQ ID NO 15
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 15

Gly Gly Gly Gly Ser
1 5

<210> SEQ ID NO 16
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 16

Gly Gly Gly Gly Ser Gly Gly Gly Gly Ser
1 5 10

<210> SEQ ID NO 17
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 17

Gly Gly Gly Gly Ser Gly Gly Gly Gly Ser Gly Gly Gly Gly Ser Gly
1 5 10 15

Gly Gly Gly Ser
20

<210> SEQ ID NO 18
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 18

Gly Gly Gly Ser Ala Ala Ala
1 5

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aagctttcat gaccagcaag 20

```
<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20

atctaagctt ctatacaata ctgattgcgg tg                                32


<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21

atcggtaccc aggtttctga tgttccgcgt                                   30


<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22

ggccaagctt ctaggtacgg tagttaatcg                                   30


<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23

agctccatgg gaagcacacg gtcacactgc t                                 31


<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24

agctgcatgc aagttagctc actcattagg ga                                32


<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25

ggtgcccata tggcgagcaa agaaaccttt acc                               33


<210> SEQ ID NO 26
<211> LENGTH: 33
<212> TYPE: DNA
<213> ORGANISM: Artificial Sequence
<220> FEATURE:
<223> OTHER INFORMATION: Primer
```

<400> SEQUENCE: 26
ccgacgggat cctcattaaa cgatgctgat tgc 33

<210> SEQ ID NO 27
<211> LENGTH: 45
<212> TYPE: PRT
<213> ORGANISM: Artificial Sequence
<220> FEATURE:
<223> OTHER INFORMATION: Synthetically generated peptide

<400> SEQUENCE: 27

Ser Gly Arg Leu Val Pro Arg Gly Ser Pro Gly Ser Gly Tyr Ile Pro
1 5 10 15

Glu Ala Pro Arg Asp Gly Gln Ala Trp Arg Lys Asp Gly Glu Trp Val
20 25 30

Leu Leu Ser Thr Phe Leu Gly His His His His His His
35 40 45

<210> SEQ ID NO 28
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 28

Arg Val Pro Pro Arg Tyr His Ala Lys Ile Ser Pro Met Val Asn
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 29

Asp Val Glu Ala Trp Leu Gly Ala Arg Val Pro Leu Val Glu Thr
1 5 10 15

<210> SEQ ID NO 30
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 30

Asp Val Glu Ala Trp Leu Gly Ala Arg
1 5

<210> SEQ ID NO 31
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 31

Gly Leu Asn Asp Ile Phe Glu Ala Gln Lys Ile Glu Trp His Glu
1 5 10 15

<210> SEQ ID NO 32
<211> LENGTH: 12
<212> TYPE: PRT
<213> ORGANISM: Artificial Sequence

```
<220> FEATURE:
<223> OTHER INFORMATION: Synthetically generated peptide

<400> SEQUENCE: 32

Gly Gly Gly Ser Gly Gly Gly Ser Gly Gly Gly Ser
 1               5                  10


<210> SEQ ID NO 33
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 33

Gly Gly Gly Gly Ser
 1               5


<210> SEQ ID NO 34
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 34

Gly Gly Gly Ser Gly Gly Gly Ser Gly Gly Gly Ser
 1               5                  10
```

MODIFIED PHAGE FOR DISPLAYING POST-TRANSLATIONALLY MODIFIED PROTEINS AND USES THEREOF

CROSS-REFERENCE TO RELATED APPLICATIONS

The present application claims priority to U.S. Provisional Application No. 60/866,710, filed Nov. 21, 2006, which is incorporated by reference herein in its entirety.

STATEMENT REGARDING FEDERALLY FUNDED RESEARCH

This invention was made with government support under Grant No. R21 AI058791 awarded by the National Institutes of Health (NIH). The government has certain rights in the invention.

TECHNICAL FIELD

The technical field relates to modified phage particles and methods of making and using the modified phage particles. More specifically, the technical field is related to modified phage particles that display post-translationally modified proteins on the surface of the phage.

BACKGROUND

Bacteriophage lambda (λ) is a dsDNA, temperate phage, 50 nm wide and about 150 nm long. Lambda can accept inserts and genomic deletions allowing for insertion of up to 15 kb (Chauthaiwale et al. 1992. Microbiol Rev 56:577-91). Finally, lambda is extremely stable under multiple storage conditions, including desiccation, and large-scale production of lambda is rapid and relatively inexpensive making it a versatile option for vaccine administration to low income nations (Jepson and March 2004. Vaccine 22:2413-9).

Lambda has been used in multiple peptide display experiments (Gupta et al. 2003. Advances in Virus Research 60:421-67; Hoess, 2002. Curr Pharm Biotechnol 3:23-8; Mikawa et al. 1996. J Mol Biol 262:21-30; Santi et al. 2000. J Mol Biol 296:497-508; Sternberg and Hoess. 1995. Proc Natl Acad Sci USA 92:1609-13). Lambda has two identified platforms for peptide display. The tail protein, gpV, consists of 32 subunits important for infection of the bacterial host. After the deletion of a nonessential region of the carboxy terminus, protein and peptide fusions can be successfully displayed on gpV in low copy numbers (Hoess, 2002. Curr Pharm Biotechnol 3:23-8). The second lambda platform for peptide display is the coat protein gpD. The gpD capsid protein is 11.4 kDa and it serves to stabilize the phage head after genomic insertion; there are between 405 and 420 copies of gpD per phage, allowing for higher copy numbers of the displayed peptide. Fusions of both the amino and carboxy terminus have been successfully displayed on the coat surface (Mikawa et al. 1996. J Mol Biol 262:21-30) but resolution of the crystal structure for gpD indicated that the carboxy terminus is well suited to peptide display (Yang, F. et al. 2000. Nat Struct Biol 7:230-7).

Sternberg and Hoess described a method for peptide display in lambda phage. Their base phage lacked gpD, but was stable due to a genomic size of 78.5% of wild type. In addition, the phage possessed a temperature sensitive mutation in the gene responsible for repressing the lytic lifecycle. Therefore, the phage could be stably grown as an *E. coli* lysogen and the lytic phage released when desired. Transformation of the lambda lysogens with a gpD-peptide expression plasmid resulted in gpD complementation of the phage in trans after lytic induction (Sternberg, N., and R. H. Hoess. 1995. Proc Natl Acad Sci USA 92:1609-13). Eguchi et al. adapted this system for gene delivery to mammalian cells (Eguchi, A. et al. 2001. J Biol Chem 276:26204-10). The Eguchi expression plasmids contained the protein transduction domain of HIV-1 Tat fused to the amino terminus of gpD. In addition, luciferase (luc) or green fluorescent protein (GFP) expression cassettes were inserted into a unique EcoRI restriction site of the lambda genome (λ, D1180) to form λ, D1180(gfp) and λ D1180(luc). Transformation and lytic induction of *E. coli* lysogens resulted in the formation of recombinant lambda displaying Tat-gpD peptide fusions and capable of delivering either GFP or luc for mammalian cell expression. Successful transduction and subsequent gene expression of COS-1 cells was demonstrated by luciferase assay and fluorescence microscopy. Site-specific GFP expression was also observed after injection of mice with $8.5\times10^9$ plaque forming units (pfu) of Tat phage (Eguchi, A. et al. 2001. J Biol Chem 276:26204-10).

Phage are inexpensive to produce and purify, are genetically tractable, and have a substantial track record of safe use in humans and research animals in large quantities for the treatment of bacterial infections (Barrow, P. et al. 1998. Clinical and Diagnostic Laboratory Immunology 5:294-8; Barrow, P. A., and J. S. Soothill. 1997. Trends Microbiol 5:268-71; Dubos, R. et al. 1943. J Exp Med 78:161-168; Schoolnik, G. K. et al. 2004. Nature Biotechnology 22:505-6). The use of phage in vaccine delivery has been proposed, but the development of phage-based vaccines has centered on phage display of antigenic peptides linked to filamentous (M13) coat proteins. These vaccines have successfully induced antibody and some cytolytic responses in laboratory animals (Chen, X. et al. 2001. Nat Med 7:1225-31, De Berardinis, P. et al. 1999. Vaccine 17:1434-41; De Berardinis, P. et al. 2000. Nat Biotechnol 18:873-6), but the T-cell response is often weaker than those observed in mammalian viral vectors. Furthermore, these approaches are limited to short antigenic epitopes, due to the constraints on surface display of peptides on filamentous phage.

Display of proteins in a dense, repetitive array results in strong humoral immune responses, as exemplified by the success of virus-like particles (VLPs) as recombinant vaccine platforms (e.g., for human papillomavirus). However, these approaches have so far failed to elicit the desired antibody response.

SUMMARY

Disclosed herein is a modified phage comprising a fusion protein located on the surface of the phage wherein the fusion protein comprises a surface protein and a post-translationally modified protein. Also disclosed are methods of making and using modified phage comprising post-translationally modified proteins.

The details of one or more embodiments are set forth in the accompanying drawings and the description below. Other features, objects, and advantages will be apparent from the description and drawings, and from the claims.

DETAILED DESCRIPTION

Figures 1, 2:
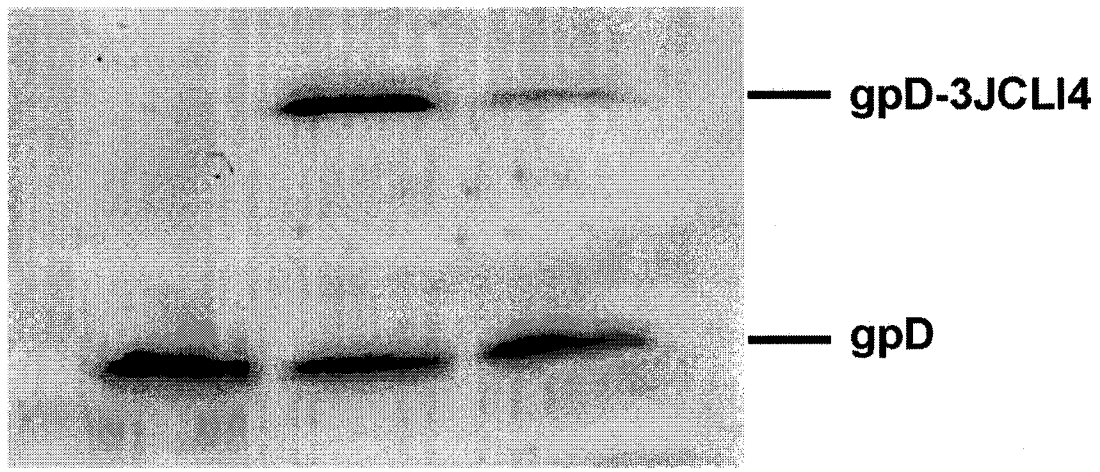
FIG. 1 shows co-expression of 3JCLI4-gpD and wild-type gpD results in the generation of mosaic phage particles. Lysogens of TOP10 cells containing gpD-deficient λ D1180 (Luc) were transformed with plasmid vectors encoding either wild-type gpD alone (gpD) or with two plasmids that permitted the co-expression of wild-type and recombinant gpD in the same *E. coli* host cell (3JCLI4 DUAL, CDF3JCLI4 DUAL). Following lysogen induction, CsCl-banding and dialysis, purified phage particles were titered on LE392 *E. coli* host cells. A total of $1\times10^9$ plaque forming units (PFU) of each preparation was then loaded on a 20% SDS-PAGE gel and phage protein content was examined by immunoblot analysis, using a rabbit polyclonal antiserum directed against gpD. Wild type gpD (approximately 12 kDa) was incorporated into all of the phage preparations, as well as inclusion of recombinant gpD-3JCLI4 (approximately 23 kDa) in preparations generated from lysogens co-transformed with both wild-type and recombinant gpD expression vectors.
FIG. 2 shows the in vitro decoration of lambda phage particles with recombinant gpD. Lambda phage particles ($2\times10^7$ PFU/lane) were boiled in SDS sample buffer and loaded onto a 15% SDS-PAGE gel. After electrophoretic separation, proteins were transferred to a nitrocellulose membrane and reacted with a gpD-specific rabbit polyclonal antiserum. Bound antibodies were then detected using a HRP-conjugated anti-rabbit antiserum. Lanes 1 is phage particles that were decorated with recombinant gpD protein in vitro and then repurified by CsCl density gradient centrifugation (Dec. (gpD+)); lane 2 is phage particles prior to in vitro decoration (Undecorated (gpD−)) and lane 3 is molecular weight markers (MWM; the kD marker is indicated, and the protein above it corresponds to a 30 kD marker).

Arrayed protein display results in strong humoral immune responses. Display of proteins or peptides in an ordered, repetitive array leads to greatly increased immune responses, compared to immunization with soluble protein antigens. This is exemplified by the success of virus-like particles (VLPs) as recombinant vaccine antigens, both for hepatitis B virus (McAleer et al., *Nature* 307:178-80 (1984) and for human papillomavirus (HPV) (Evans et al., *J. Infect. Dis.* 183:1485-93 (2001), Harper et al., *Lancet* 364:1757-65 (2004), Harper et al., *Lancet* 367:1247-55 (2006), VIIIa et al., *Lancet Oncol.* 6:271-8 (2005)). Bacteriophage particles permit the display of short, exogenous peptides at high copy number in a quasicrystalline array that facilitates antibody production through cross-linking of surface immunoglobulins. However, bacterial host cells do not encode the machinery necessary to permit post translational modification of proteins such as glycosylation, which poses a problem when attempting to display mammalian post-translationally modified proteins on the surface of a bacteriophage vector.

Described herein are phage capsids as a simple structural scaffold to display post-translationally modified proteins such as glycoproteins in a highly immunogenic context. This is accomplished using an in vitro complementation system, in order to "decorate" phage particles with mammalian cell-derived proteins.

Bacteriophage have been experimentally administered to animals and safely used in humans for several decades, both for the treatment of bacterial infections and also for the assessment of humoral immune responses in immuno-compromised subjects. The development of phage display technology has made it possible to display short peptides on the capsid of filamentous bacteriophage (Scott and Smith, *Science* 249:386-90 (1990), Smith, *Science* 228:1315-7 (1985)), leading to the evaluation of phage display vectors as potential vaccine delivery platforms (Barrow and Soothill, *Trends Microbiol.* 5:268-71 (1997), Hoess, *Curr. Pharm. Biotechnol.* 3:23-8 (2002), Merril et al., *Nat. Rev. Drug Discov.* 2:489-97 (2003), Monaci et al., *Curr. Opin. Mol. Ther.* 3:159-69 (2001), Sulakvelidze et al., *Antimicrob. Agents Chemother.* 45:649-59 (2001)). These phage vectors have considerable advantages over other vaccine platforms, such as mammalian virus vectors, due to their genetic tractability, inexpensive production and suitability for scale-up (Chen and Lim, *J. Biotechnol.* 51:1-20 (1996)), as well as their physical stability and compatibility with simple storage and formulation methods such as desiccation (Jepson and March, *Vaccine* 22:2413-9 (2004)).

Bacteriophage λ is a temperate phage with a double-stranded genome of approximately 48 kb encapsulated in an icosahedral capsid (approximately 50 nm in diameter) with a long, fibrous tail (approximately 150 nm in length). The λ capsid is composed of two major coat proteins, gpE and gpD. Lambda capsid maturation begins with the formation of the prohead, composed solely of gpE. As the genomic DNA is packaged, the capsid expands in volume by about 45% and roughly 405 copies of gpD are then added to fully populate and stabilize the capsid.

Foreign peptides and proteins can be displayed at high copy number on the surface of λ phage particles, by fusing them to the gpD major coat protein (Eguchi et al., *J. Biol. Chem.* 276:26204-10 (2001), Gupta et al., *J. Mol. Biol.* 334:241-54 (2003), Maruyama et al., *PNAS* 91:8273-7 (1994), Piersanti et al., *J. Mol. Med.* 82:467-76 (2004), Santi et al., *J. Mol. Biol.* 296:497-508 (2000), Sternberg and Hoess, *PNAS* 92:1609-13 (1995), Yang et al., *Nat. Struct. Biol.* 7:230-7 (2000)). GpD is a trimeric, 109 amino acid protein (excluding the initial methionine which is removed from the mature protein) and is required for the packaging of full-length genomes. Lambda differs from filamentous phage vectors in that only short peptides can generally be displayed at high copy number on filamentous phage vectors. A second key difference is that gpD-deficient λ capsids can be "decorated" in vitro with exogenously supplied gpD (Hoess, *Curr. Pharm. Biotechnol.* 3:23-28 (2002)). This permits considerable flexibility with respect to the surface display of complex antigens such as the HIV-1 envelope spike. As demonstrated herein, the high-density, repeating array of displayed antigen on the surface of the phage lambda capsid results in strong humoral immune responses, greatly enhancing the immunogenicity of the protein being displayed.

Rao and colleagues have recently described an antigen decoration system using bacteriophage T4 (Sathaliyawala et al., *J. Virol.* 80:7688-98 (2006)). This bacteriophage T4 system also uses an in vitro assembly approach to display foreign proteins on the surface of a bacteriophage capsid, by fusing proteins of interest to Hoc, a nonessential T4 outer capsid protein that is present at 155 copies per phage particle (Ren and Black, *Gene* 215:439-44 (1998)). The T4/Hoc system has been used to display p24 Gag on the phage surface (Sathaliyawala et al., *J. Virol.* 80:7688-98 (2006)). The present system differs from this work in that only small, bacterially-derived fusion proteins were displayed on the surface of their T4 phage particles. In contrast, the present system provides methods for displaying on the phage scaffold post-translationally modified proteins such as glycoproteins produced in mammalian cells. Thus, the present system provides modified phage particles comprising a dense display of post-translationally modified proteins, which results in an improvement in the magnitude and/or quality of the evoked humoral immune response. Second, the present system provides a phage scaffold for the display of post-translationally modified proteins and the elicitation of stronger or more broadly reactive neutralizing antibody responses.

Provided is a modified phage comprising a post-translationally modified polypeptide displayed on the surface of the phage. As used herein, modified refers to any alteration(s) in a naturally occurring entity (e.g., a molecule) that affects either form or function. As used herein, surface polypeptide or protein refers to a polypeptide or protein that is expressed by and exposed on the phage surface. A molecule is optionally displayed on the surface of the phage by conjugating the molecule to a surface polypeptide.

The term peptide, polypeptide, protein or peptide portion is used broadly herein to mean two or more amino acids linked by a peptide bond. The term fragment is used herein to refer to a portion of a full-length peptide, polypeptide or protein. It should be recognized that the terms peptide or polypeptide are not used herein to suggest a particular size or number of amino acids comprising the molecule and that a peptide or polypeptide can contain several amino acid residues or more.

Lambda has two identified surface polypeptides that serve as platforms for peptide display. The surface polypeptide of the provided lambda phage is gpD, gpV or both. The gpD and gpV surface polypeptides have the amino acid sequence of SEQ ID NO:1 and SEQ ID NO:2, respectively. Modifications within the gpD or gpV amino acid sequences include insertions, deletions, truncations, substitutions (including conservative amino acid substitutions). Thus, provided herein are modified forms of gpD and gpV. Thus, the gpD surface polypeptide is encoded, for example, by the nucleic acid sequence of SEQ ID NO:3. The gpD surface polypeptide is optionally encoded by a codon-optimized version of SEQ ID NO:3 using techniques and procedures readily available to one skilled in the art (Gao, W. et al. 2004. Biotechnol Prog 20:443-448; Fuglsang, A. 2004. Protein Expr Purif 31; 247-249; Bradel-Tretheway, B. G. et al. 2003. J Virol Methods 111:145-156; Grosjean, H. and Fiers, W. 1982. Gene 18:199-209). Thus, the gpD surface polypeptide is encoded by the nucleic acid sequence of SEQ ID NO:4. The gpV surface polypeptide is encoded, for example, by the nucleic acid sequence of SEQ ID NO:5. The gpV surface polypeptide is optionally encoded by a codon-optimized version of SEQ ID NO:5. Further provided herein are nucleic acids that encode the modified gpD and gpV amino acid sequences.

As disclosed herein, the surface polypeptide is optionally a homolog derived from a closely related phage. Thus, the surface polypeptide is optionally gpShp from lambda-like phage 21, which shares 49% amino acid identity to gpD (Wendt J L, Feiss M. 2004. Virology 326:41-6). The known gpShp surface polypeptide has the amino acid sequence of SEQ ID NO:6 and is encoded, for example, by the relevant nucleic acid sequence contained within SEQ ID NO:7. As provided herein, the gpShp encoding nucleic acid or gpShp amino acid is optionally modified by insertions, deletions, truncations or substitutions as for gpD and gpV.

Any of the surface polypeptides are optionally a chimeric polypeptide comprising portions of gpD, gpV and/or gpShp, for example, the N-terminus of gpD or gpV and the C-terminus of gpShp or any other combination thereof.

The surface polypeptide is optionally a mutated coat protein such as a lambda E capsid protein (including, for example, the amino acid sequence of SEQ ID NO:8). Thus, the lambda E capsid protein optionally comprises, for example, an E to K substitution at residue 158 of SEQ ID NO:8 (SEQ ID NO:9), as described in the long-circulating Argo1 and Argo2 mutants of bacteriophage lambda by Merril (Merril, C. R. et al. 1996. Proc Natl Acad Sci USA 93:3188-3192). Lambda E capsid proteins and variants are used, optionally, with insertions, deletions, truncations or substitutions as for gpD and gpV.

The modified phage herein comprises a plurality of a fusion polypeptide comprising a surface polypeptide and a heterologous polypeptide displayed on the surface of the phage wherein the heterologous polypeptide is a post-translationally modified protein. As used herein the term plurality refers to more than one polypeptide. Thus, the modified phage optionally comprises a plurality of a first fusion polypeptide located on the surface of the phage, wherein the first fusion polypeptide comprises a first surface polypeptide and a first heterologous polypeptide, wherein the heterologous polypeptide is a post-translationally modified polypeptide. Thus, the phage optionally comprises a plurality of a second fusion polypeptide located on the surface of the phage wherein the second fusion polypeptide comprises a second surface polypeptide and a second heterologous polypeptide. The second surface polypeptide is the same as the first surface polypeptide or different from the first polypeptide. The first or second surface polypeptide is optionally gpV or gpD or fragments or modifications thereof.

As described herein, the phage comprises any post-translationally modified protein such as, for example, a glycopolypeptide or proteoglycan. Post-translational modifications are the result of the action of mammalian or insect host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine, and amidation of the C-terminal carboxyl.

Suitable post-translationally modified proteins for display on the phage described herein include, but are not limited to, glutaminyl modified polypeptides, asparaginyl modified polypeptides, deamidated polypeptides, hydroxylated polypeptides, phosphorylated polypeptides, methylated polypeptides, ubiquitinated polypeptides, glycosylated polypeptides and acetylated polypeptides. Suitable glycosylated polypeptides or glycopolypeptides include, but are not limited, hemagglutinin and envelope glycoproteins. Hemagglutinins (HAs) are glycoproteins found on the surface of viruses and bacteria. There are at least 16 different HAs including subtypes H1 through H16. H1, H2 and H3 are found on human influenza viruses. Another HA of interest is H5 found on the avian flu virus H5N1. For example, the heterologous polypeptide comprises any HA from subtype H1 through H16. Thus the heterologous polypeptide comprises H5 HA or H7 HA. Suitable glycoproteins also include virus glycoproteins. Viral glycoproteins include, but are not limited to, Dengue virus envelope glycopolypeptide, hepatitic C virus envelope glycopolypeptide E1, hepatitis C virus envelope glycopolypeptide E2, hantavirus envelope glycopolypeptide G1, hantavirus envelope glycopolypeptide G2. The hantavirus envelope glycopolypeptides G1 and G2 are optionally from the Andes, Hantaan or Sin Nombre strain of hantavirus. Viral glycopolypeptides also include human cytomegalovirus glycopolypeptide B, human cytomegalovirus glycopolypeptide H, human herpesvirus-8 glycopolypeptide B, human herpesvirus-8 glycopolypeptide H, human metapneumovirus glycopolypeptide F, human metapneumovirus glycopolypeptide G, human parainfluenzavirus humagglutinin-neuraminidase, human parainfluenzavirus fusion glycopolypeptides, Nipah virus glycopolypeptide F, Nipah virus glycopolypeptide G, respiratory syncytial virus glycopolypeptide F, respiratory syncytial virus glycopolypeptide G, Severe Acute Respiratory Syndrome (SARS) virus spike glycopolypeptide, West Nile virus envelope glycopolypeptide and HIV-1 envelope glycopolypeptide. The HIV-1 envelope glycopolypeptide is optionally YU2 Env, SF162 Env, Env from HIV-1 B strain, Env from HIV-1 C strain and Env from HIV-1 M strain.

In addition to the fusion polypeptide, the modified phage optionally further comprises at least one wild type surface polypeptide. As used herein, the term wild type surface polypeptide refers to a surface polypeptide as found in nature or that is not fused to a heterologous polypeptide.

The modified phage described herein optionally comprises a plurality of a fusion polypeptide comprising a surface polypeptide and a heterologous molecule wherein the heterologous polypeptide is an immunostimulatory molecule. The surface polypeptide optionally comprises gpD or gpV. Thus, the fusion polypeptide comprising an immunostimulatory molecule optionally comprises gpV. Suitable immunostimulatory molecules include, but are not limited to, B-cell activating molecules, Toll-like receptor ligands and CD 40 ligands. Thus, immunostimulatory molecules include, but are not limited to, pan allelic DR epitope (PADRE), CD40 bp and Langerhans cell-targeting peptide (LTP). Toll-like receptor ligands include, but are not limited to, flagellin. B-cell activating molecules include, but are not limited to, complement receptor 2 binding proteins such as C3d. CD 40 receptor ligands, include, but are not limited to, CD40L and CD40-binding peptides (see, U.S. Pat. No. 6,472,510, which is hereby incorporated by reference in its entirety at least for its disclosure related to CD40 binding peptides). Immunostimulatory molecules also include the RN-peptide (RVPPRYHAKISPMVN (SEQ ID NO:28), which is a pentadecapeptide that mimics muramyl peptide, and functions as an adjuvant in vivo.

Provided herein are methods for displaying post-translationally modified proteins on the surface of phage and modified phage made by the disclosed methods. The method comprises providing a host cell comprising an expression vector, wherein the expression vector comprises a nucleic acid encoding a fusion polypeptide and wherein the fusion polypeptide comprises a surface polypeptide and a heterologous polypeptide capable of being post-translationally modified; culturing the host cell under conditions that allow the host cell to express the fusion polypeptide and that allow the heterologous polypeptide to be post-translationally modified; isolating the fusion polypeptide and incubating the phage with the fusion polypeptide to form modified phage with the post-translationally modified proteins on the phage surface.

Optionally, the method comprises transforming a host cell with an expression vector, wherein the expression vector comprises a nucleic acid encoding a fusion polypeptide and wherein the fusion polypeptide comprises a surface polypeptide and a heterologous polypeptide capable of being post-translationally modified. Thus, the method optionally comprises transforming a host cell with an expression vector, wherein the expression vector comprises a nucleic acid encoding a fusion polypeptide and wherein the fusion polypeptide comprises a surface polypeptide and a heterologous polypeptide capable of being post-translationally modified; culturing the host cell under conditions that allow the host cell to express the fusion polypeptide and that allow the heterologous polypeptide to be post-translationally modified; isolating the fusion polypeptide and incubating the phage with the fusion polypeptide to form modified phage with the post-translationally modified proteins on the phage surface. The phage are optionally incubated with the fusion polypeptides in a cell free system. The method optionally comprises incubating or culturing the phage with wild-type surface polypeptides in addition to the fusion polypeptides.

The host cell is any host cell capable of expressing the fusion polypeptide and post-translationally modifying the heterologous polypeptide. Thus, the host cell is a eukaryotic host cell. Thus, the host cell is a mammalian host cell or an insect host cell. Such host cells are known to those of skill in the art. Suitable host cells are obtained, for example, from the American Type Culture Collection (ATCC), 10810 University Boulevard, Manassas, Va. 20110-2209, U.S.A. The host cell is optionally transformed using one or more expression vectors encoding a plurality of fusion polypeptides as desired. As used herein the term expression vector is a vector capable of expressing a polypeptide or protein.

The host cell is optionally transformed using a plasmid construct encoding a plurality of fusion polypeptides. A single plasmid comprises 1, 2, 3, 4, 5, 6, 7, 8, 9, 10 or more unique fusion polypeptides. The transformation step of the method is performed using a plurality of plasmids that each encode one or more fusion polypeptides. A single eukaryotic host cell optionally comprises 1, 2, 3, 4, 5, 6, 7, 8, 9, 10 or more unique plasmids that each encode the one or more unique fusion polypeptides as discussed above. Thus, for example, the eukaryotic host cell comprises a first plasmid and a second plasmid, wherein the first and second plasmids each encode the same or a different fusion polypeptide. Alternatively, the eukaryotic host cell comprises one plasmid that encodes at least two different fusion polypeptides.

Provided herein are expression vectors comprising a nucleotide sequence that encodes any of the fusion polypeptides provided herein, wherein the nucleotide sequence is operably linked to an expression control sequence for expression in eukaryotic host cells. Preferred promoters controlling transcription from vectors in mammalian host cells are obtained from various sources, including, for example, from the genomes of viruses (e.g., polyoma, Simian Virus 40 (SV40), adenovirus, retroviruses, hepatitis-B virus and cytomegalovirus), or from heterologous mammalian promoters, (e.g. beta actin promoter or EF1 promoter), or from hybrid or chimeric promoters (e.g., cytomegalovirus promoter fused to the beta actin promoter). The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lucky, M. L. et al., Mol. Cell. Bio. 3: 1108 (1983)) to the transcription unit. Furthermore, enhancers are optionally within an intron (Banerji, J. L. et al., Cell 33: 729 (1983)) as well as within the coding sequence itself (Osborne, T. F. et al., Mol. Cell. Bio. 4: 1293 (1984)). They are usually between 10 and 300 by in length, and they function in cis. Enhancers function to increase transcription from nearby promoters. Enhancer sequences of mammalian genes (globin, elastase, albumin, fetoprotein and insulin) and from eukaryotic cell virus are used. Eukaryotic cell virus enhancers include the SV40 enhancer on the late side of the replication origin (bp 100-270), the cytomegalovirus early promoter enhancer, the polyoma enhancer on the late side of the replication origin, and adenovirus enhancers.

The promoter and/or enhancer are optionally activated specifically either by light or specific chemical events which trigger their function. Systems are regulated by reagents such as tetracycline and dexamethasone, synthetic transcription factors, directed RNA self-cleavage (Yen L. et al. 2004. Nature 431:471-476), and other approaches. There are also ways to enhance viral vector gene expression by exposure to irradiation, such as gamma irradiation, or alkylating chemotherapy drugs.

The promoter and/or enhancer region act as a constitutive promoter and/or enhancer to maximize expression of the region of the transcription unit to be transcribed. Optionally, the promoter and/or enhancer region is active in all eukaryotic cell types, even if it is only expressed in a particular type of cell at a particular time. A preferred promoter of this type is the CMV promoter (650 bases). Other preferred promoters are SV40 promoters, cytomegalovirus (plus a linked intron sequence), beta-actin, elongation factor-1 (EF-1) and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. The transcription unit optionally contains a polyadenylation region. One benefit of this region is that it increases the likelihood that the transcribed unit will be processed and transported like mRNA. The identification and use of polyadenylation signals in expression constructs is well established. Homologous polyadenylation signals are optionally used in the transgene constructs. In certain transcription units, the polyadenylation region is derived from the SV40 early polyadenylation signal and consists of about 400 bases. The certain transcribed units contain other standard sequences alone or in combination with the above sequences to improve expression from, or stability of, the construct.

Vectors optionally include a nucleic acid sequence encoding a marker product. This marker product is used to determine if the gene has been delivered to the cell and if, once delivered, the gene is being expressed. Marker genes include, for example, green fluorescent protein (GFP) and luciferase. The marker is optionally a selectable marker. Examples of selectable markers for mammalian cells include dihydrofolate reductase (DHFR), thymidine kinase, neomycin, neomycin analog G418, hygromycin, and puromycin. When such selectable markers are successfully transferred into a mammalian host cell, the transformed mammalian host cell survives if placed under selective pressure whereas non-transformed cells do not.

There are between 405 and 420 copies of gpD per phage, allowing for high copy numbers of a displayed peptide. Therefore a fusion polypeptide comprising the gpD protein is expressed 405-420 times on the surface of each particle, increasing the likelihood of the peptide forming a stable interaction with its target. In some cases, the peptide density is lowered using a mosaic phage approach, wherein a combination of modified and unmodified surface proteins are expressed by the phage.

The ratio of surface polypeptides is adapted using standard methods known in the art. For example, combinations of high- and low-copy origins of replication are optionally used. As another example, programmed frameshifting elements or suppressable termination codons (in combination with an appropriate suppressor tRNA) are used such that the nucleic acid encoding the surface polypeptide for which lower expression is desired is expressed in stoichiometrically titered levels, relative to the wild-type protein. Thus, the modified and unmodified surface polypeptides are expressed in cis or in trans.

The ratio of surface polypeptides are regulated by expressing 2 or more such peptides using plasmids with transcriptional promoters of different strength or with inducible promoter elements. The ratio of surface polypeptides are regulated by expressing 2 or more such peptides using genes that contain introduced suppressible translational stop codons, ribosome shifting sequencing, or codon sequences that have been altered to be either more or less optimal for host cells. As used herein, the term host cell or host cells refer to eukaryotic cells like mammalian or insect host cells.

The ratio of surface polypeptides are optionally regulated by expressing 2 or more such peptides in the same mammalian or insect host cell, using plasmids that are maintained at different copy numbers. Plasmid replicons that are carried by plasmid vectors and are used in this fashion include elements that result in low copy number plasmid maintenance, medium copy number plasmid maintenance and high copy number plasmid maintenance. Use of origin elements from different complementation groups permit simultaneous expression of many different modified surface polypeptides within a single host cell.

The display of multiple different surface polypeptides on the same lambda phage particle result in the generation of mosaic phage. Mosaic derivatives of filamentous phages, including Type 3+3 phagemid systems for low copy number display on the pIII protein, and Type 88 vectors for multivalent display on the major coat protein, pVIII, are known to those skilled in the art. These systems rely upon co-expression of wild-type and recombinant pVIII from a single phage genome (Type 88 vectors), or expression of wild-type pIII by helper phage, and recombinant pIII by a phagemid (Type 3+3 vectors). As disclosed herein, mosaic phage are generated using a coat-protein deficient phage genome that is complemented in trans, using one or many plasmid expression vectors to achieve a very high diversity of different possible combinations of surface polypeptides on the surface of each phage particle that is produced. The present system also has improved biocontainment and safety. This is because of the use of a replication-defective lambda host (containing, for example, a deletion of the phage gpD gene), combined with the use of a non-homologous, codon-altered gpD cassette, for example, in the complementing plasmid expression construct(s). This minimizes any potential for recombination between the lambda genome and the complementing plasmid.

It is also possible to insert multiple modifying peptides within a single surface polypeptide. For example, the molecular structure of gpD shows it to be highly flexible, in terms of its ability to accept extended exogenous peptide sequences at both its N and C terminus (Yang, F. et al. 2000. Nat Struct Biol 7:230-7). This approach is optionally further enhanced through the use of flexible linker peptides.

Thus, provided herein is modified phage and methods of making a modified phage comprising a fusion protein comprising a surface polypeptide and a post-translationally modified polypeptide wherein the surface polypeptide and the post-translationally modified polypeptide are separated by one or more flexible linker polypeptides. Linker polypeptides include ($Gly_4Ser$)n (SEQ ID NO:33). Linker polypeptides also include, for example, alternating Serine and Glycine stretches exemplified by $(GGGGS)_3$ (SEQ ID NO:10) (Freund C. et al. 1993. FEBS Lett 320:97-100), $(GGGS)_3$ (SEQ ID NO:34), $(GSGSGS)_n$(SEQ ID NO:11), and G(SGGG)$_2$SGGT (SEQ ID NO:12); the flexible linker peptide of *Trichoderma reesi* cellobiohydrolase I (CBHI) (Takkinen, K. et al. 1991. Prot Eng 4:837-841); and elbow-like peptides such as SAKTTP (SEQ ID NO:13), RADAAP (SEQ ID NO:14), and derivatives thereof (see Le Gall F. et al. 2004. Protein Eng Des Sel 17:357-366, which, along with other references cited herein, is incorporated herein by reference in its entirety for all linkers and derivatives thereof and methods of making same). Thus, the linker polypeptide is, for example, $(Gly_4Ser)_i$ (SEQ ID NO:15), $(Gly_4Ser)_2$ (SEQ ID NO:16), $(Gly_4Ser)_3$ (SEQ ID NO:10), $(Gly_4Ser)_4$ (SEQ ID NO:17) and $Gly_3Ser\ Ala_3$ (SEQ ID NO:18).

The phage surface polypeptide is optionally linked to a wild-type and/or post-translationally modified polypeptide by one or more streptavidin binding moieties to create an avidin-biotin bridge that couples a peptide or protein of interest to the phage surface. Streptavidin binding moities include, but are not limited to, Nano-tag, which is a high affinity streptavidin-binding peptide. Full-length Nano-tag is a 15 amino acid peptide, DVEAWLDERVPLVET (SEQ ID NO:29) that binds streptavidin with a dissociation constant of 4 nM. Variants of this peptide include DVEAWLGARVPLVET (SEQ ID NO:29) (WT 7G8A; Kd=4.1 nM) and DVEAWLGAR (SEQ ID NO:30) (C-6 7G8A; Kd=17 nM). Both of these peptides are well-tolerated when fused to foreign proteins.

The phage surface polypeptide is optionally linked to the wild-type and/or post-translationally modified polypeptide by one or more biotin binding moieties. Such biotinylation recognition seqeuces include, but are not limited to, AviTag, which is a peptide substrate for the BirA biotin ligase. AviTag is a 15 amino acid peptide (GLNDIFEAQKIEWHE; (SEQ ID NO:31)) that is biotinylated in vivo upon concurrent expression of the BirA biotin ligase. Filamentous phage particles that display the AviTag are efficiently biotinylated in vivo in *E. coli* host cells that overexpress the BirA ligase and are optionally biotinylated in vitro using purified BirA, which is available from Avidity LLC, Denver, Colo.

The Nano-tag or AviTag are fused to either the N- or C-terminus of gpD, with a short flexible linker ([GGGS]3 (SEQ ID NO:32)) separating the tag from gpD. Then the efficiency of recombinant protein expression in *E. coli* host cells and the ability of the recombinant gpD fusion proteins to complement a gpD-deficient lambda lysogen (as measured by phage titers, following lytic induction of the gpD-deficient lambda lysogen and subsequent purification of phage particles from the induced cultures) is assessed.

All of the vectors described above optionally comprise additional nucleic acids fused to a surface polypeptide. Thus it will be appreciated that the vectors optionally include any of a number of genes of interest, combinations of genes of interest and genes of interest/regulatory element combinations. Thus, a fusion protein optionally comprises a therapeutic gene including, but not limited to, cytokines or interferons (such as GMCSF, TNF-alpha, IFN-gamma), chemokines (such as MIP3-alpha, chemerin or short peptides derived therefrom), co-stimulatory molecules (such as CD40, CD40L, CD80, CD86) and allogeneic HLA molecules (such as HLA B7).

Provided herein are also variants, modifications or derivatives of the disclosed fusion polypeptides, surface polypeptides and/or post-translationally modified polypeptides. It is understood that one way to define any variants, modifications, or derivatives of the disclosed genes and proteins herein is through defining the variants, modification, and derivatives in terms of similarity to specific known sequences. As used herein, "homolog" refers to a polypeptide or nucleic acid with similarity to a specific known sequence. Specifically disclosed are variants of the nucleic acids and polypeptides herein disclosed which have at least 40, 41, 42, 43, 44, 45, 46, 47, 48, 49, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent similarity to the stated or known sequence. Those of skill in the art readily understand how to determine the similarity of two proteins or nucleic acids. For example, the similarity can be calculated after aligning the two sequences so that the similarity is at its highest level.

Another way of calculating similarity is performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference in their entirety for the methods of calculating similarity.

The same types of similarity are obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

In addition, protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule but deletion can range from 1-30 residues. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues but can occur at a number of different locations at once; insertions usually will be on the order of about from 1 to 10 amino acid residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place.

Provided herein are methods of eliciting an immune response to post-translationally modified polypeptide in a subject comprising administering a modified phage comprising the post-translationally modified polypeptide on the surface of the phage to the subject. The post-translationally modified polypeptide is optionally coupled to the surface of the phage by a biotin-avidin bridge. The method optionally comprises administering an immunostimulatory molecule selected from the group consisting of interferons, cytokines, chemokines an soluble ligands for CD40 receptor. Such molecules and their methods of administration are well known to those of skill in the art.

The provided phage is used in heterologous prime-boost vaccination regimens, thereby reducing the cost of immunization (due to the low cost of phage vectors) while also increasing its effectiveness (by eliciting improved immune responses) (Amara, R. R. et al. 2001. Science 292:69-74, Degano, P. et al. 1999. Vaccine 18:623-32; M. et al. 1998. Eur J Immunol 28:4345-55; Schneider, J. et al. 1999. Immunol Rev 170:29-38). It is understood that one can effectively utilize various combinations of phage vectors and mammalian viral vectors, as well as phage plus recombinant protein, and phage plus DNA plasmid vectors, in successful immunization regimens. Such regimens also include synthetic or natural adjuvants, including molecularly designed approaches (cytokines, cytokine-encoding plasmids/vectors), Toll-like receptor (TLR) ligands, and the use of chemokines and other molecules intended to recruit and activate dendritic cells (Barouch, D. H. et al. 2000. Science 290:486-92; Chen, K. et al. 1997. Cancer Research 57:3511-6; Lore, K. et al. 2003. J Immunol 171:4320-8; Moore, A. C. et al. 2002. J Virol 76:243-50).

The method optionally comprises administering to the subject Toll-like receptor ligand. CpG oligonucleotides that interact with Toll-like receptor-9 (TLR9) increase immunogenicity (Utaisincharoen, P. et al. 2003. Clin Exp Immunol 132:70-5) and engagement of other TLRs (West, M. A. et al. 2004. Science 305:1153-7). Thus, provided herein is the use of CpG oligonucleotides and other small molecule ligands of mammalian TLRs to enhance immunogenicity. Several CpG oligonucleotides and TLR ligands have already been developed for human use and/or tested in human clinical trials, including CpG 7909, resiquimod (R-848) and related molecules (developed by 3M) and other similar materials (Cooper, C. L. et al. 2004. Vaccine 22:3136-43; Lore, K. et al. 2003. J Immunol 171:4320-8; Sauder, D. N. et al. 2003. Antimicrob Agents Chemother 47:3846-52). CpG7909 can be synthesized with a wholly phosphorothioate backbone. In this form, it can be used safely in humans (Cooper, C. L. et al. 2004. Vaccine 22:3136-43).

Provided are also pharmaceutical compositions comprising the modified phage herein. Thus, the herein provided phage are administered in vitro or in vivo in a pharmaceutically acceptable carrier. By pharmaceutically acceptable is meant a material that is not biologically or otherwise undesirable, i.e., the material is administered to a subject, along with the vector, without causing undesirable biological effects or interacting in a deleterious manner with any of the other components of the pharmaceutical composition in which it is contained. The carrier is selected to minimize any degradation of the active ingredient and to minimize any adverse side effects in the subject.

The compositions are administered orally, parenterally (e.g., intravenously), by intramuscular injection, by intraperitoneal injection, intradermally, transdermally, extracorporeally, topically or the like, including topical intranasal administration or administration by inhalant. For example, provided is a method of eliciting an immune response in a subject, comprising intradermally administering to the subject a modified phage provided herein. It has also been shown that lambda is capable of withstanding the harsh conditions encountered during oral administration (Jepson, C. D. and J. B. March. 2004. Vaccine 22:2413-9). Orally administered phage reaches the bloodstream for multiple species of bacteriophage (Hildebrand, G. J. and H. Wolochow. 1962. Proc Soc Exp Biol Med 109:183-5; Reynaud, A. et al. 1992. Vet Microbiol 30:203-12; Weber-Dabrowska, B. et al. 1987. Arch Immunol Ther Exp 35:563-8). Furthermore, specific targeting peptide sequences allow phage to pass through the intestinal wall and thereby enter the general circulation (Duerr, D. M. et al. 2004. J Virol Methods 116:177-80).

Pharmaceutical compositions include carriers, thickeners, diluents, buffers, preservatives and surface active agents in addition to the molecule of choice. Pharmaceutical carriers are known to those skilled in the art. These most typically would be standard carriers for administration of drugs to humans, including solutions such as sterile water, saline, and buffered solutions at physiological pH. Suitable carriers and their formulations are described in Remington: The Science and Practice of Pharmacy (21st ed.) eds. A. R. Gennaro et al., University of the Sciences in Philadelphia 2005. Typically, an appropriate amount of a pharmaceutically-acceptable salt is used in the formulation to render the formulation isotonic. Examples of a pharmaceutically-acceptable carriers include, but are not limited to, saline, Ringer's solution and dextrose solution. Further carriers include sustained release preparations such as semipermeable matrices of solid hydrophobic polymers containing the phage, which matrices are in the form of shaped articles, e.g., films, liposomes or microparticles. It will be apparent to those skilled in the art that certain carriers may be more preferable depending upon, for instance, the route of administration and concentration of composition being administered.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

As used herein, topical intranasal administration means delivery of the compositions into the nose and nasal passages through one or both of the nares and can comprise delivery by a spraying mechanism or droplet mechanism, or through aerosolization of the nucleic acid or vector. Administration of the compositions by inhalant is through the nose or mouth via delivery by a spraying or droplet mechanism. Delivery is optionally directly to any area of the respiratory system (e.g., lungs) via intubation.

Formulations for topical administration include ointments, lotions, creams, gels, drops, suppositories, sprays, liquids and powders. Conventional pharmaceutical carriers, aqueous, powder or oily bases, thickeners and the like are optionally necessary or desirable.

Compositions for oral administration include powders or granules, suspensions or solutions in water or non-aqueous media, capsules, sachets, or tablets. Thickeners, flavorings, diluents, emulsifiers, dispersing aids or binders are optionally desirable.

Generally phage particles are transferred to a biologically compatible solution or pharmaceutically acceptable delivery vehicle, such as sterile saline, or other aqueous or non-aqueous isotonic sterile injection solutions or suspensions, numerous examples of which are well known in the art, including Ringer's, phosphate buffered saline, or other similar vehicles.

The phage can be administered in a number of ways depending on whether local or systemic treatment is desired, and on the area to be treated. Delivery of the recombinant phage is carried out via any of several routes of administration, including, topical, oral, parenterally, intravenously, intraperitoneally, intramuscularly, subcutaneously, intracavity, transdermally, intrahepatically, catheterization (including cardiac catheterization), intracranially, nebulization/inhalation, or by instillation via bronchoscopy.

Parenteral administration of the composition, if used, is generally characterized by injection. Injectables are prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein for the methods taught therein.

The pharmaceutical compositions described herein optionally comprise an adjuvant. Suitable adjuvants include, but are not limited to, alum, TLR agonists, saponin derivatives, Ribi, AS04, montanide and ISA 51. Suitable TLR agonists include TLR9 agonists such as a CpG oligonucleotides, imiquimod, resiquimod and MPL-A. Suitable saponin derivatives include QS21 and GPI0100.

The pharmaceutical compositions optionally comprise an immunostimulatory molecule selected from the group consisting of interferons, cytokines, chemokines and soluble ligands for CD40 receptor.

The modified phage is optionally used to elicit an antigenic response to treat infectious or acquired diseases. These diseases include viral infections (e.g., influenza, HIV/AIDS), bacterial infections (e.g., bacterial meningitis), parasitic infections (e.g., fungal infections), neurological diseases (e.g., Alzheimer's disease) and cancer. Examples of such antigens include HIV-1 Env, Gag, Pol, Tat, Rev, Vif, Vpr and Nef, as well HCMV gB and gH/gL, influenzavirus HA and NA proteins, *M. tuberculosis* proteins ESAT6 and HSP65, malarial proteins such as thrombospondin-related adhesion protein (TRAP), and many more. Examples of viral pathogens subject to control by vaccines include HIV-1, hepatitis B and C viruses, cytomegalovirus, Dengue virus, respiratory syncytial virus, the SARS coronavirus, Ebolavirus, Lassa, influenzavirus, and others. Examples of bacterial pathogens and antigens of interest include bacterially-encoded toxins and toxin-related molecules (such as the anthrax edema factor (EF), lethal factor (LF) and protective agent (PA) as well as botulinum toxin, and virulence factors and toxins encoded by *Fransicella tularensis, Yersinia pestis* and other biodefense agents. Other known antigens include surface, structural, regulatory or enzymatic proteins from malarial parasites and *Mycobacterium tuberculosis*, or from other medically important pathogens. The antigenic response is sufficient to induce a protective humoral or cellular immune response in the subject.

Effective dosages of phage depends on a variety of factors and varies somewhat from subject to subject. Effective dosages and schedules for administering the compositions is determined empirically, and making such determinations is within the skill in the art. The exact amount required varies from subject to subject, depending on the species, age, weight and general condition of the subject, the severity of the disease being treated, the particular virus or vector used and its mode of administration. Thus, it is not possible to specify an exact amount for every composition. However, an appropriate amount is determined by one of ordinary skill in the art given the guidance provided herein.

The dosage ranges for the administration of the compositions are those large enough to produce the desired effect in which the symptoms of the disease are affected or prevented. The dosage is not so large as to cause adverse side effects, such as unwanted cross-reactions and anaphylactic reactions. The dosage is adjusted by the individual physician in the event of any counter indications. Dosage varies, and can be administered in one or more dose administrations daily, for one or several days.

Following administration of a disclosed composition the efficacy of the composition is assessed in various ways well known to the skilled practitioner. For instance, one of ordinary skill in the art will understand that a composition disclosed herein is efficacious in eliciting an immune response in a subject by observing a humoral response. For example, the immune response to phage particles at either high or low density is assessed in animals.

As described herein, the immunogenicity of post-translationally modified proteins is improved by display at high density on a repetitively ordered scaffold. As described below in the Examples, expression vectors encoding translational fusions between the major lambda phage coat protein, gpD, and the influenzavirus hemagglutinin (HA) have been constructed. The influenzavirus H5 hemagglutinin was constructed to form a stabilized trimer HA:gpD fusion protein that was expressed in insect cells. After protein purification, the biochemical and conformational properties of the HA:gpD fusion proteins were characterized and used to decorate preformed, gpD-deficient phage capsids. The density of HA antigen display varied by generating mosaic phage particles that display differing ratios of wild-type gpD and recombinant gpD (HA:gpD).

The immune response to lambda phage particles displaying post-translationally modified polypeptides at either high or low density is assessed, for example, in animals such as, for example, guinea pigs or ferrets. Animals are immunized and then the magnitude and quality of the antigen-specific antibody response are measured using binding assays. The analyses of virus-neutralizing activity are performed against both homologous and heterologous strains. Ordered, dense display of post-translationally modified polypeptides on the lambda phage scaffold allows for generation of improved antibody responses to the post-translationally modified polypepitdes.

The surface HIV-1 envelope glycoprotein subunit, gp120, is a major target for virus-neutralizing antibodies, but immunization with recombinant forms of gp120 fails to elicit broadly neutralizing antibodies and monomeric gp120 failed to demonstrate protective efficacy in a recently completed Phase III clinical trial (Gilbert et al., *J. Infect. Dis.* 191:666-677 (2005)). Elicitation of broadly reactive neutralizing antibodies remains an important goal in HIV-1 vaccine design and development.

The immunogenicity of HIV-1 envelope spikes is limited, in part, as a result of their sparse and irregular distribution on the virion surface. Phage lambda provides a solution to this problem by increasing the immunogenicity of Env by displaying Env at high density on a repetitively ordered scaffold (provided by phage particle). Env display can be achieved using a simple in vitro complementation system, to "decorate" phage particles with soluble Env oligomers, produced in eukaryotic cells.

As an example, the method comprises constructing expression vectors encoding translational fusions between the major lambda phage coat protein, gpD, and a glycoprotein such as, for example, HIV-1 Env. Two different Env antigens (e.g., YU2 and SF162 or variant thereof) are used to construct Env:gpD fusion proteins, that are expressed in eukaryotic cells. After protein purification, the biochemical and conformational properties of the Env:gpD fusion proteins are characterized and used to decorate preformed, gpD-deficient phage capsids. Thus, the phage optionally comprises YU2 and/or SF162 or variants thereof on the surface of the phage. The density of antigen display are optionally varied by generating mosaic phage particles that display differing ratios of wild-type gpD and recombinant gpD (Env:gpD).

Mammalian expression vectors encoding translational fusions between gpD and HIV-1 Env are optionally constructed using stabilized HW Envgp140 trimers based on the neutralization-resistant YU2 primary R5HIV-1 isolate and soluble trimeric Envgp 140 constructs derived from SF162.

Cleavage-deficient, trimeric HIV-1 Envgp140 expression constructs are optionally used to generate mammalian expression constructs that encode Env:gpD fusion proteins. The constructs are used to create and produce a translational fusion protein in which gpD is fused to the C-terminus of HIV-1 Envgp140. Analogous constructs containing the murine C3d complement component at the C-terminus of HIV-1 Envgp140 are conformationally authentic and capable of eliciting virus-neutralizing responses (Bower et al., *J. Virol.* 78:4710-9 (2004), Green et al., *J. Virol.* 77:2046-55 (2003), Ross et al., *AIDS Res. Hum. Retroviruses* 17:829-35 (2001)).

Expression constructs are made in which HIV-1 Envgp140 is translationally fused to a short flexible linker peptide at its C-terminus, and then to a human codon-optimized version of gpD and a terminal His6 tag for purification. The general arrangement of such expression constructs is as follows:

PROMOTER->(tPA leader)-(post-translationally modified)-(trimerizing fibritin foldon)-(spacer)-(gpD)-His6-[STOP]

This strategy places post-translationally modified protein at the N-terminus of gpD. GpD is known to accept large protein inserts on both its N- and C-termini, and the presence of these exogenous sequences does not interfere with the ability of gpD to bind the phage capsid. Without meaning to be limited by theory, this may be because the capsid binding region within gpD maps to a structurally disordered region that is little affected by neighboring protein subdomains.

The expression constructs are optionally human codon-optimized or non-optimized.

The authenticity and functional/conformational integrity of the fusion proteins described herein is determined by several assays known to those of skill in the art. For example, immunoblot assays are performed with antibodies directed against the heterologous polypeptides and against the surface polypeptide. In addition, the molecular weight of the fusion protein is confirmed when analyzed by gel filtration. Additional methods of analysis include, but are not limited to, immunoprecipitation assays and ELISA analysis, using specific antibodies.

GpD-deficient phage capsids are optionally generated by thermal induction of a λD1180 lysogen that contains a genome of approximately 80% of the wild-type size and then purified using CsCl-density gradient centrifugation and dialyzed extensively against SM buffer. GpD-deficient phage are infectious and physically stable in the absence of gpD, provided that the phage genome is between 78 and 82% of wild-type size. However, such phage remain exquisitely sensitive to inactivation by EDTA. Therefore, the successful display of gpD fusion proteins on the phage surface can be determined by measuring phage titers on *E. coli* host cells, such as LE392 cells in the presence and absence of EDTA. If there is a <5-fold decline in phage titer following exposure to 100 mM EDTA, this is representative of suitable phage. Suitable assays also include immunoblot analysis and ELISA analysis.

Lambda phage particles are optionally subjected to tuning-fork based atomic force microscopy (AFM) using frequency modulation to directly observe post-translationally modified spikes. This technique allows for resolution of objects as small as 1 nm diameter (e.g. carbon nanotubes). This method is used to confirm, using direct inspection, that fusion proteins have been successfully incorporated onto the surface of lambda phage particles.

It is usually also necessary to control the endotoxin (ET) content of the phage preparations. ET levels are measured using the limulus amebocyte lectin (LAL) assay (Cambrex Corporation, East Rutherford, N.J.). If initial levels are >10 EU/ml, the phage preparations are repurified over an EndoTrap Red endotoxin removal column (Cambrex Corporation, East Rutherford, N.J.); this affinity matrix efficiently removes bacterial endotoxin from aqueous solutions containing low or high molecular weight substances, and is compatible with phage storage buffer. Several cycles of such purification are performed, as necessary. Generation of endotoxin-free phage particles are performed, for example, as described in Boratynski et al., *Cell Mol. Biol. Lett.* 9:253-9 (2004). In addition, endotoxin are removed by alternative chromatography resin or mixing-centrifugation method to remove endotoxin (Zhang et al., *Biotechnol. Prog.* 21:1220-5 (2005)). Phage lots should contain less than 10 EU of endotoxin per ml, as measured by the LAL assay. This is a low target level of endotoxin, which is readily achievable with phage vectors (Boratynski et al., Cell Mol. Biol. Lett. 9:253-9 (2004)).

The immune response to lambda phage particles is determined at either high or low density using an animal model, such as, for example, mice or guinea pigs. Animals are immunized and then the magnitude and quality of the post-translationally modified-specific antibody response is measured using, for example, ELISA, avidity assays, and analyses of virus-neutralizing activity (directed against both homologous and heterologous strains). Immune responses can be compared to those elicited by phage that displays only wild-type gpD on its surface.

The modified phage described herein are optionally used to produce antibodies specific for the post-translationally modified polypeptide. Antibodies directed specifically against post-translationally modified polypeptide have a wide number of uses, including for constructing immunoassays, for use in tissue and cellular immunocytochemistry, for characterizing polypeptide domains, for use as markers, and for the screening of cDNA expression libraries. As used herein the terms antibody and immunoglobulin are used interchangeably. The term antibodies is used herein in a broad sense and includes both polyclonal and monoclonal antibodies. In addition to intact immunoglobulin molecules, useful herein are fragments, chimeras, or polymers of immunoglobulin molecules, as long as they are chosen for their higher specificity for a post-translationally modified polypeptide as compared to their specificity for the polypeptide in the absence of the post-translational modification. The antibodies are tested for their desired activity using in vitro assays, or by analogous methods, after which their in vivo therapeutic or prophylactic activities can be tested according to known clinical testing methods.

Libraries of antibodies or active antibody fragments are optionally generated and screened using the modified phage described herein using method as described in, for example, U.S. Pat. No. 5,804,440 to Burton et al. and U.S. Pat. No. 6,096,441 to Barbas et al., which are incorporated herein by reference in their entireties at least for their methods for using phage to generate antibodies.

Monoclonal antibodies include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired activity.

Monoclonal antibodies are made using any procedure which produces monoclonal antibodies. For example, disclosed monoclonal antibodies are prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes are immunized in vitro.

Monoclonal antibodies are optionally made by recombinant DNA methods. DNA encoding the disclosed monoclonal antibodies are readily isolated and sequenced using conventional procedures (e.g., by using oligonucleotide probes that are capable of binding specifically to genes encoding the heavy and light chains of murine antibodies).

Digestion of antibodies to produce fragments thereof, particularly, Fab fragments, are accomplished using routine techniques known in the art. For instance, digestion is performed using papain. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The fragments, whether attached to other sequences, optionally include insertions, deletions, substitutions, or other selected modifications of particular regions or specific amino acids residues, provided the activity of the antibody or antibody fragment is not significantly altered or impaired compared to the non-modified antibody or antibody fragment. These modifications optionally provide for some additional property, such as to remove/add amino acids capable of disulfide bonding, to increase its bio-longevity, to alter its secretory characteristics. In any case, the antibody or antibody fragment must possess a bioactive property, such as specific binding to its cognate antigen. Functional or active regions of the antibody or antibody fragment are identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the terms antibody or antibodies also refer to a human antibody and/or a humanized antibody. Many non-human antibodies (e.g., those derived from mice, rats, or rabbits) are naturally antigenic in humans and thus can give rise to undesirable immune responses when administered to humans. Therefore, the use of human or humanized antibodies in the methods serves to lessen the chance that an antibody administered to a human will evoke an undesirable immune response.

Human antibodies are obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551 255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ line mutant mice results in complete inhibition of endogenous antibody production, and the successful transfer of the human germ line antibody gene array into such germ line mutant mice results in the production of human antibodies upon antigen challenge.

Methods for humanizing non human antibodies are well known in the art. For example, humanized antibodies are generated by substituting rodent CDRs or CDR sequences for the corresponding sequences of a human antibody. Methods that are optionally used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.). Antibody humanization techniques generally involve the use of recombinant DNA technology to manipulate the DNA sequence encoding one or more polypeptide chains of an antibody molecule. Accordingly, a humanized form of a non human antibody (or a fragment thereof) is a chimeric antibody or antibody chain that contains a portion of an antigen binding site from a non-human (donor) antibody integrated into the framework of a human (recipient) antibody. As used throughout, antibody fragments include Fv, Fab, Fab', or other antigen binding portion of an antibody.

Disclosed are materials, compositions, and components that are used for, used in conjunction with, used in preparation for, or are products of the disclosed methods and compositions. These and other materials are disclosed herein, and it is understood that when combinations, subsets, interactions, groups etc. of these materials are disclosed that while specific reference of each various individual and collective combinations and permutation of these compounds may not be explicitly disclosed, each is specifically contemplated and described herein. For example, if a phage is disclosed and discussed and a number of modifications that can be made to a number of molecules including the phage are discussed, each and every combination and permutation of the phage and the modifications that are possible are specifically contemplated unless specifically indicated to the contrary. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Unless defined otherwise, all technical and scientific terms used herein have the same meanings as commonly understood by one of skill in the art to which the disclosed method and compositions belong. Publications cited herein and the material for which they are cited are hereby specifically incorporated by reference.

Throughout the description and claims of this specification, the word comprise and variations of the word, such as comprising and comprises, means including but not limited to, and is not intended to exclude, for example, other additives, components, integers or steps.

It is to be understood that the disclosed method and compositions are not limited to specific synthetic methods, specific analytical techniques, or to particular reagents unless otherwise specified, and, as such, may vary. It is also to be understood that the terminology used herein is not intended to be limiting. Note the headings used herein are for organizational purposes only and are not meant to limit the description provided herein or the claims attached hereto.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

EXAMPLES

Example 1

A Method for Displaying Recalcitrant Proteins on the Surface of Bacteriophage Lambda Bacteriophage λ can accommodate the display of large exogenous peptides and proteins on the gpD major coat protein. However, some proteins cannot readily be displayed at high copy number (405 copies per capsid). To solve this problem, a dual expression system was developed in which gpD deficient lysogens can be simultaneously complemented with both wild-type and recombinant forms of gpD. As a first step, an *E. coli* codon-optimized (ECO) derivative of the wild-type λ gpD gene was synthesized. The ECO-gpD gene was then inserted into the prokaryotic expression plasmid pTrc (creating plasmid pTrc-gpD), and a gene cassette corresponding to a desired fusion partner (3JCLI4) was inserted as a C-terminal fusion to gpD, to create pTrc-gpD-3JCLI4. 3JCLI4 is a genetically engineered derivative of the tenth fibronectin type III domain, which has nanomolar affinity for the cellular αvβ3 integrin receptor.

Lambda D1180 (Luc) genomes contain a mammalian expression cassette that encodes for firefly luciferase under the transcriptional control of the human cytomegalovirus immediate early promoter. An *E. coli* codon-optimized (ECO) derivative of the wild-type λ gpD gene was generated synthetically (GeneArt, Regensburg, Germany) and inserted into the pTrcHis plasmid (Invitrogen, Carlsbad, Calif.). The optimized sequence was selected on the basis of Entelechon's proprietary gene design software (http://www.entelechon.com/), which performs codon optimization for the species of interest, while avoiding specified restriction enzyme sites. The corresponding sequence is available via GenBank, with the accession number DQ156943. The resulting construct, pTrc-gpD-fusion contained the codon-optimized gpD sequence (with its authentic ATG codon, but without a translational stop codon), followed by a short flexible linker sequence [$G(SGGG)_2SGGT$, SEQ ID NO:12] and then by BamHI and KpnI restriction sites; desired fusion partners of interest were inserted between the KpnI site and a terminal HindIII site. Note that, during the process of cloning, the native, promoter-proximal NcoI site within pTrc was eliminated. Other linker sequences that can be used include, but are not limited to, alternating Serine and Glycine stretches exemplified by $(GGGGS)_3$ (SEQ ID NO:10) (Freund C. et al. 1993. FEBS Lett 320:97-100), $(GSGSGS)_n$(SEQ ID NO:11), and $G(SGGG)_2SGGT$ (SEQ ID NO:12); the flexible linker peptide of *Trichoderma reesi* cellobiohydrolase I (CBHI) (Takkinen, K. et al. 1991. Prot Eng 4:837-841); and elbow-like peptides such as SAKTTP (SEQ ID NO:13), RADAAP (SEQ ID NO:14), and derivatives thereof (Le Gall F. et al. 2004. Protein Eng Des Sel 17:357-366).

In order to derive a construct that expressed gpD alone, the gpD insert was subjected to polymerase chain reaction (PCR) amplification using primers that added a translational stop codon at the 3' end of the gpD gene. The oligonucleotide primers used for this amplification were: (i) gpD-StopFOR (5'-aagattcATGaccagcaag-3', SEQ ID NO:19) and (ii) gpD-StopREV (5'-atctaagcttCTAtacaatactgattgcggtg-3', SEQ ID NO:20); underlined sequences denote the added BspHI and HindIII sites, respectively, while capitalized boldface letters denote the ATG codon and inserted translational stop codon, respectively. The resulting PCR product was restricted with BspHI and HindIII and then inserted into the parental pTrc vector using the NcoI and HindIII restriction sites, to create pTrc-gpD.

A series of plasmid constructs were created in which specific sequences of interest were fused to gpD. The exogenous DNA sequences chosen included an insert encoding for a high-affinity $\alpha_v\beta_3$ binding protein derived from the tenth fibronectin type III domain (3JCLI4) (Richards, J. et al. (2003)). This was PCR amplified from an available parental plasmid (Richards, J. et al. (2003)), using the following primers: 3JCLI4FOR (5'-atcggtacccaggtttctgatgttccgcgt-3', SEQ ID NO:21) and 3JCLI4REV (5'-ggccaagcttCTAggtacggtagttaatcg-3', SEQ ID NO:22). The PCR product was then digested with KpnI and HindIII (these sites are underlined in the primer sequences) and inserted into the corresponding restriction sites of our pTrc-gpD-fusion vector, so as to create pTrc-gpD-3JCLI4.

In order to create plasmid vectors that permit expression of two different forms of gpD within the same *E. coli* host cell, the pBR322-derived pMB1 origin of DNA replication in the pTrc-based expression plasmids (approximately 20 copies/chromosome equivalent; Bolivar, F. et al. (1977); Brosius, J. et al. (1982)) was replaced with a compatible origin of DNA replication derived from the CloDF13 replicon (approximately 20-40 copies/chromosome equivalent; Nijkamp, H. J. et al. (1986); Kim, J. S. and Raines, R. T. (1993)). The CDF-derived origin and flanking antibiotic resistance marker were amplified by PCR from the pCDF-1b plasmid (Novagen, San Diego, Calif.), using CDFDUETFOR (5'-agctccatgggaagcacacggtcacactgct-3', SEQ ID NO:23) and CDFDUETREV (5'-agctgcatgcaagttagctcactcattaggga-3', SEQ ID NO:24), digested with SphI and NcoI (these sites are underlined in the primer sequences), and then inserted into the SphI and BspHI sites in pTrc and its derivatives. All gpD-encoding plasmids containing the pBR322 or CDF origins of replication also carry the ampicillin or spectinomycin antibiotic resistance genes, respectively.

Lysogens of TOP10 cells (Invitrogen, Carlsbad, Calif.) containing λ D1180 (Luc) (Eguchi, A. et al. (2001)) were transformed with pTrc plasmids encoding either wild-type gpD alone, gpD-3JCLI4 alone, or the combination of wild-type gpD plus gpD-3JCLI4. Lysogens containing the coat protein plasmids were grown to mid-log phase at 32° C. in the presence of antibiotics (ampicillin or spectinomycin, 50 μg/mL, Sigma). The lysogens, which contain a temperature-sensitive mutation in the cI repressor, were then induced by increasing the culture temperature to 45° C. for approximately 15 minutes. After induction, cultures were incubated at 38° C. for an additional 3 hours to allow for phage replication and assembly. Cells were then collected by centrifugation and lysed with chloroform (Sigma). DNAse I (Worthington Biochemical Corporation, Lakewood, N.J.) was added to a final concentration of 10 μg/mL to remove any contaminating nucleic acids, and lysed cultures were cleared of debris by centrifugation; phage were pelleted from the supernatant by ultracentrifugation. The resulting pellet was resuspended in phage suspension media (100 mM NaCl, 10 mM MgSO4, 50 mM Tris-Cl (pH 7.5), 0.1% gelatin) and further purified by cesium chloride density gradient ultracentrifugation. The resulting phage bands were pulled from the gradient using a syringe and 18 G needle and dialyzed against 10 mM NaCl, 50 mM Tris-Cl (pH 7.5), and 10 mM MgCl2. Phage preparations were titered on LE392 (supE, supF) *E. coli* host cells (Stratagene, La Jolla, Calif.).

The authentic (non codon-optimized) λ phage gpD gene was amplified by PCR from pAT101 (Yang, F. et al. (2000); Forrer, P. and Jaussi, R. (1998)) using the gpD forward primer (5'-ggtgcccatatggcgagcaaagaaacctttacc-3', SEQ ID NO:25) and the gpD reverse primer (5'-ccgacgggatcctcattaaacgatgctgattgc-3', SEQ ID NO:26) and then cloned into the pET15b plasmid (Novagen, San Diego, Calif.) using the NdeI and BamHI restriction sites (underlined). The resulting pET15b-gpD plasmid was transformed into BL21 cells (Invitrogen, Carlsbad, Calif.). Transformed bacteria were grown to mid-log phase and then induced for 3 hours with IPTG added to a final concentration of 1 mM. Cells were pelleted by centrifugation, lysed with BugBuster (Novagen, San Diego, Calif.), and treated with BENZONASE® and lysozyme (Novagen, San Diego, Calif.) according to the manufacturer's recommendations. The resulting lysate was clarified by centrifugation and temporarily stored at −20° C. Thawed lysate was purified using a $Co^{2+}$ column (BD TALON™; BD Biosciences Clontech, Mountain View, Calif.) according to the manufacturer's recommendations. The eluted fractions were analyzed by polyacrylamide gel electrophoresis (PAGE), followed by immunoblot analysis using an anti-His5 antibody reactive with the His6-tag that had been added to the gpD protein. Approximately 3 mg of PAGE purified gpD protein was used to raise a polyclonal antiserum in rabbits (Sigma Genosys, The Woodlands, Tex.). The reactivity of the resulting antiserum against gpD was confirmed by immunoblot analysis, and the antiserum was then preserved in 0.02% sodium methiolate and stored in aliquots at −80° C. until use.

$1\times10^9$ plaque forming units (PFU) of CsCl-banded phage particles were combined with 2×SDS loading buffer and heated to 95° C. for 5 minutes. Samples were separated on a 20% SDS-PAGE gel. Proteins were then transferred to a nitrocellulose membrane and incubated with the polyclonal anti-gpD anti-serum at a dilution of 1:1000 (in 1×PBS/0.1% Tween (PBST) containing 5% nonfat dry milk). After washing with PBST, the nitrocellulose membrane was incubated with HRP-conjugated donkey anti-rabbit antibody (Amersham, Piscataway, N.J.) at a dilution of 1:3000 (also in PBST containing 5% nonfat dry milk). HRP-conjugated antibody was detected using ECL-Plus substrate (Amersham, Piscataway, N.J.). Blots were imaged using the ChemiDoc XRS chemiluminescence chamber and Quantity One software version 4.5.2 (BioRad, Hercules, Calif.).

In order to generate plasmids capable of efficiently expressing gpD in *E. coli* host cells, an *E. coli* codon-optimized (ECO) derivative of the wild-type λ gpD gene was synthesized. The *E. coli* codon-optimized gene has greatly reduced homology to its native λ counterpart (only 78% nucleotide identity), which can effectively eliminate the potential for homologous DNA recombination between the ECO-gpD sequence and its native λ phage counterpart, thereby reducing the possibility that a complementing gpD plasmid might recombine with a gpD-deficient λ lysogen.

The ECO-gpD gene was inserted into pTrc to create pTrc-gpD, and a sequence cassette corresponding to the desired fusion partner (3JCLI4) was then inserted as a C-terminal fusion to gpD, to create pTrc-gpD-3JCLI4. Additionally, constructs were generated in which the pBR322 origin of replication in the pTrc-based vectors was replaced with the CDF origin of replication, to yield pTrc-gpD-CDF and pTrc-gpD-3JCLI4-CDF. Protein expression from each of these constructs was confirmed by immunoblot analysis of IPTG-induced bacterial cell lysates using a gpD-specific rabbit antiserum; the constructs were then transformed into 2 D1180 lysogens, in order to examine their ability to complement this gpD-deficient phage strain and thereby permit recovery of infectious phage particles.

Lysogens of TOP10 cells containing λ D1180 (Luc) were transformed with either the pTrc-gpD-3JCLI4 or pTrc-gpD expression plasmid, encoding the gpD-3JCLI4 fusion protein or wild-type gpD, respectively. Following heat induction, cell lysis and cesium chloride density gradient ultracentrifugation of a 1 liter preparation, no phage particles could be recovered from the lysogens that had been transformed with the plasmid vector encoding the recombinant gpD-3JCLI4 coat protein fusion, as reflected by the absence of the characteristic λ phage band in the cesium chloride density gradient. In contrast, when the λ D1180 (Luc) lysogens were transformed with a plasmid encoding wild-type gpD, infectious phage particles were readily recovered.

These results indicated that the gpD-3JCLI4 fusion protein either interfere with phage assembly or prevent the formation of stable phage particles. To resolve this unexpected difficulty, the gpD-3JCLI4 fusion protein was expressed on the surface of phage λ through the use of a mosaic approach, in which the final virion contained a mixture of both wild-type and recombinant gpD subunits.

Lysogens of TOP10 cells containing λ D1180 (Luc) were co-transformed with plasmids encoding both recombinant and wild-type forms of gpD. This was achieved using a set of gpD expression vectors that contained one of two origins of replication—either the pBR322-derived pMB1 origin (pBR-ori) or a second compatible, low-copy origin derived from pCDF-1b (CDF-ori). Lysogens were then cotransformed with either (i) a pBR-ori based plasmid encoding a recombinant form of gpD (pTrc-gpD-3JCLI4) plus a CDF-ori based plasmid encoding wild-type gpD (pTrc-gpD-CDF), or (ii) a CDF-ori based plasmid encoding a recombinant form of gpD (pTrc-gpD-3JCLI4-CDF) plus a pBR-ori based plasmid encoding wild-type gpD (pTrc-gpD). Following heat induction of the lysogen, cell lysis, and cesium chloride density gradient ultracentrifugation, phage containing the gpD-3JCLI4 fusion protein that had previously proven recalcitrant was efficiently recovered, as reflected by the presence of a characteristic phage band in the CsCl gradient.

These recombinant phage preparations were collected from the CsCl gradient, dialyzed, and titered on LE392 *E. coli* host cells. All of the phage preparations, including the mosaic phages were found to be infectious. The titers of the mosaic phages were generally similar to those of wild-type phage preparations (i.e., gpD-deficient phage that were complemented using wild-type gpD alone), although it was noted that use of the pBR-based gpD fusion constructs resulted in somewhat lower titers of the mosaic phage, as compared to their CDF-based counterparts.

An aliquot ($1\times10^9$ PFU) of each of these phage preparations was extracted, separated on a 20% SDS-PAGE gel, and subjected to immunoblot analysis using the rabbit polyclonal antiserum against gpD. The phage preparations that were derived from lysogens that had been cotransformed with wild-type and recombinant gpD expression plasmids contained two distinct forms of gpD consistent with their being gpD-mosaic phages (compare results for gpD wild-type to those for the other constructs shown in FIG. 1). It was also noted that use of the pBR-based gpD fusion constructs resulted in slightly greater levels of recombinant gpD into the phage particles, as compared to the CDF-based plasmids (compare results for 3JCLI4 DUAL with those for CDF3JCLI4 DUAL; FIG. 1).

Example 2

In Vitro Decoration of gpD-Deficient Phage with a Recombinant Form of Wild Type gpD GpD is usually required for the generation of stable lambda phage particles containing wild-type length genomes. It is possible to package genomes of sub-genomic length in the absence of gpD, provided that (i) the genome is between approximately 78% and 82% of wild-type length, and (ii) exogenous Mg2+ ions are provided to negate the charge interactions that otherwise lead to head instability. GpD-deficient phage particles, once produced, are highly unstable in the presence of EDTA (which chelates out divalent cations) but can be readily "decorated" with gpD in vitro simply by exposing the phage to a crude lysate of *E. coli* cells that includes recombinant gpD protein. When gpD deficient phage are mixed with exogenous gpD in this fashion, the exogenous gpD is rapidly incorporated into the phage head; this results in the generation of EDTA-stable phage particles that can be re-purified by CsCl density gradient centrifugation.

To decorate gpD-deficient phage particles with exogenous gpD, gpD-deficient phage particles (with a genome size of approximately 80% of wild-type) were produced. The particles were then mixed with recombinant His6-tagged gpD protein (purified to ~90% homogeneity from *E. coli* cell lysates by metal ion chromatography) or with buffer alone (control preps) and subjected to CsCl density gradient centrifugation. Equal amounts of phage particles were then subjected to immunoblot analysis using a gpD-specific antiserum (FIG. 2). The results revealed that only the "decorated" phage preparation contained detectable amounts of gpD.

Example 3

Figure 3:
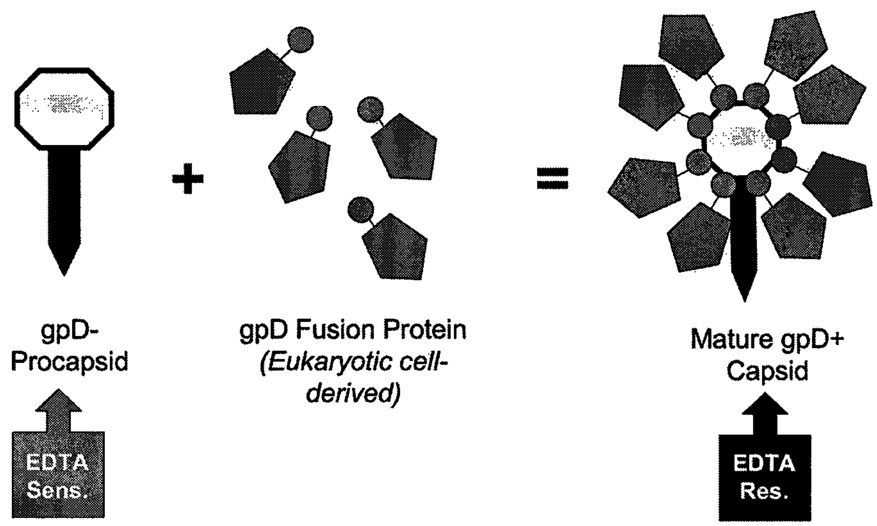
FIG. 3 is a schematic representation of phage decoration. For example, gpD-deficient phage capsids were mixed with exogenously supplied recombinant gpD fusion protein, derived from either insect cells or other eukarotic host cells. The exogenously produced recombinant gpD molecules occupy available binding sites on the phage capsid (405 sites/capsid), thereby decorating the preformed phage scaffold. This stabilizes the phage capsid, rendering it EDTA-resistant. Phage capsids without a full complement of gpD remain EDTA-sensitive and are rapidly inactivated in the presence of EDTA.

In Vitro Decoration of gpD-Deficient Phage with a Recombinant gpD:Glycoprotein Fusion Molecule Produced in Insect Cells The strategy for generation of phage particles displaying a recombinant gpD:glycoprotein is shown in FIG. 3. Displayed glycoprotein in this study was a trimeric form of the H5N1 influenza A virus hemagglutin molecule. As FIG. 3 shows, gpD-deficient phage is highly sensitive to EDTA, while phage particles that display a full complement of gpD on their surface are EDTA-resistant. This is because EDTA chelates out divalent metal cations that are required for stabilization of the gpD-deficient phage capsid.

Figure 4:
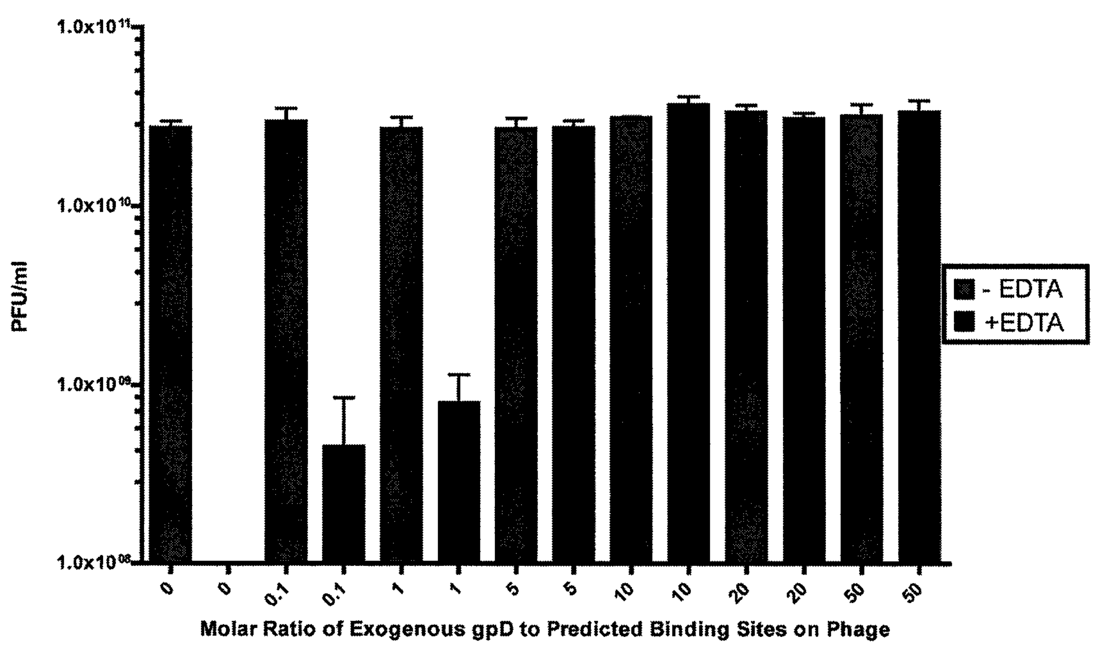
FIG. 4 is a graph showing a titration analysis to define optimum conditions for decoration of pre-formed, gpD-deficient, phage capsids with exogenously supplied gpD. gpD-deficient phage particles were incubated in vitro for 20 minutes at 30° C. with varying amounts of gpD:His6 (gpD), corresponding to the indicated molar ratio of exogenous gpD to predicted gpD binding sites on the phage population being decorated. A ratio of zero (0) corresponds to gpD-deficient phage capsids with no exogenous gpD. The phage particles were then exposed to EDTA (100 mM; lanes marked plus (+)) or left in SM buffer (lanes marked minus (−)) for 15 minutes at 37° C. The phage were then added to LE392 *E. coli* host cells, and titered by plaque assay. The results show that a 5-fold molar excess of exogenous gpD is sufficient to fully occupy all available binding sites on the phage population being decorated resulting in complete resistance to EDTA. Below this level, phage remained incompletely decorated and at least partially EDTA-sensitive. Results represent mean values for an experiment that was performed in triplicate; error bars denote the standard deviation.

Experiments were performed using wild-type gpD (gpD-His6) to determine the molar ratio of exogenous gpD to available binding sites on the gpD-deficient phage capsid that are required for efficient in vitro decoration of phage particles with exogenously provided gpD. The results are shown in FIG. 4. As FIG. 4 shows, when the molar ratio of exogenous gpD to available gpD binding sites on the phage capsid was 5 or higher, decoration was highly efficient—as reflected by the resistance of the resulting capsids to EDTA. Note that the data shown in FIG. 4 represent mean phage titers from an experiment performed in triplicate; bars denote the standard deviation of these values.

In order to display a recombinant gpD; glycoprotein on the phage capsid, the hemagglutinin molecule from a H5N1 strain of human influenza A virus was expressed in insect cells. Like HIV-1 Env, the influenza virus HA is trimeric. An insect cell codon-optimized gene cassette was constructed that encoded the lambda phage coat protein, fused to the ectodomain of the influenza A virus H5 hemagglutinin in insect cells, together with an exogenous trimerization motif (the fibritin foldon; denoted FT3) and a terminal His6 tag for protein purification (on the C-terminus of the protein). The resulting recombinant H5 HA ectodomain was secreted into the cell culture medium because it was fused in-frame to an insect cell signal peptide (present in plasmid pAcGP67A [BD Pharmingen]). The final translational fusion construct had an overall organization as follows (Secretion signal)-(gD)-(flexible spacer)-(H5 HA Ectodomain)-FT3-HA Tag-[STOP].

This fusion protein was then expressed in insect cells (*T. ni*) using a baculovirus vector, and purified by nickel ion chromatography. After elution from the column, and dialysis against SM buffer (the buffer in which phage particles are stored), the material was analyzed by denaturing, reducing SDS-PAGE and Coomassie blue staining. This analysis (FIG. 5) revealed that the protein was purified to >95% homogeneity, with a yield on the order of 2-5 mg/L of insect cell culture.

The recombinant gpD:HA protein was used to decorate gpD-deficient phage particles. GpD-deficient phage particles were mixed with (i) recombinant gpD:His6 alone, (ii) recombinant gpD:HA protein alone, (iii) a 1:1 mixture of recombinant gpD:His6 plus gpD:HA or (iv) buffer alone (control preps).

Exposure to 100 mM EDTA resulted in a dramatic reduction in the infectious titer of gpD-deficient phage (by almost 3 logs, relative to untreated phage). However, EDTA treatment had no effect on the titer of phage particles that had been incubated in the presence of wild-type gpD:His6 (see FIG. 6; this is denoted as gpD). This result shows that the phage particles were successfully "decorated" by this protein, and that the phage capsid was therefore protected against the effects of EDTA.

Figure 6:
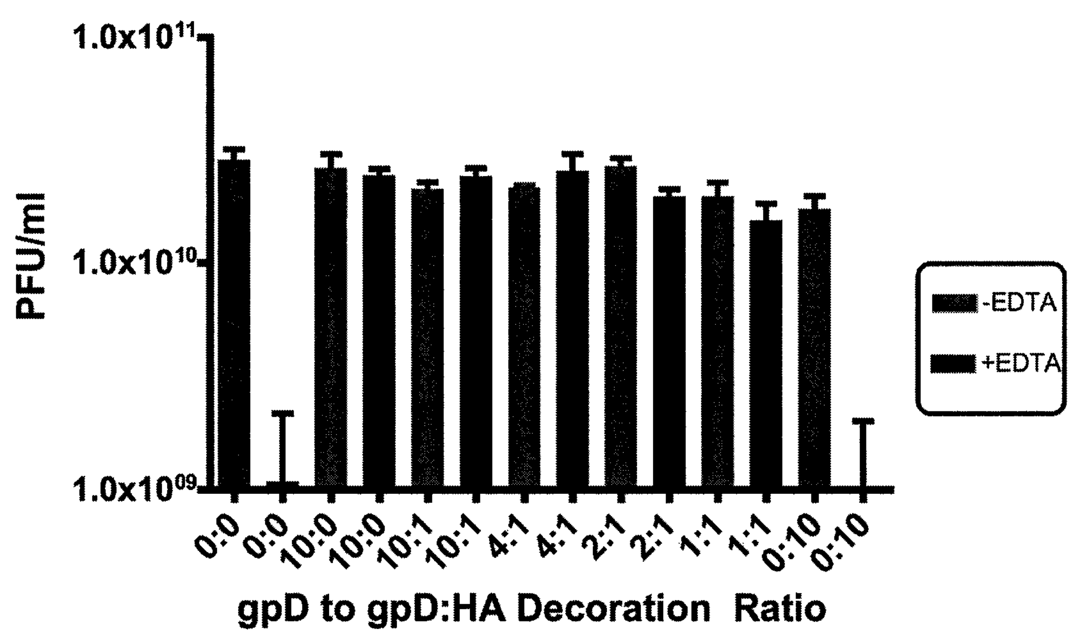
FIG. 6 is a graph showing a titration analysis to define optimum conditions for decoration of pre-formed, gpD-deficient, phage capsids with exogenously supplied gpD:HA fusion protein. gpD-deficient phage particles were incubated in vitro for 20 minutes at 30° C. with varying molar ratios of gpD:His6 (gpD) and gpD:HA fusion protein (gpD:HA). The phage particles were then exposed to EDTA (100 mM; lanes marked plus (+)) or left in SM buffer (lanes marked minus (−)) for 15 minutes at 37° C. After this, the phage were added to LE392 *E. coli* host cells and titered by plaque assay. Results represent mean values for an experiment that was performed in triplicate; error bars denote the standard deviation.

Addition of gpD:HA also resulted in near-complete resistance of phage particles to EDTA. Since EDTA resistance requires the presence of an almost complete complement of gpD on the phage surface, this result shows that, when present as the only available form of gpD, the gpD:HA protein occupies almost all of the available binding sites on the phage capsid. The fact that the gpD:HA decorated phage remained slightly sensitive to EDTA (as indicated by the ~5-fold drop in phage titer, following EDTA treatment; FIG. 6) suggests either that a few gpD binding sites may remain unoccupied or, more likely, that steric hindrance between the bulky gpD:HA trimers may occur and that this may slightly destabilize the phage capsids.

This problem can be overcome by generating mosaic phage particles that displayed both wild-type and recombinant gpD on their surface (see FIG. 2). The mosaic approach was tested to determine if it might be similarly effective in the context of gpD:HA.

The optimum molar ratio of wild-type gpD (gpD:His6) to gpD:HA fusion protein required for efficient decoration of phage particles was determined in a systematic fashion. gpD deficient phage were mixed with wild-type gpD and gpD:HA fusion protein, at various ratios. The resulting mosaic decorated phage particles were then tested for EDTA sensitivity. Specifically, gpD-deficient phage particles were incubated in vitro for 20 minutes at 30° C. with varying molar ratios of gpD:His6 (gpD) and gpD:HA fusion protein (gpD:HA). A ratio of zero to zero (0:0) corresponds to gpD-deficient phage capsids with no exogenous gpD, while ratios of ten to zero (10:0) and zero to ten (0:10) correspond to gpD-deficient phage capsids that were decorated with either wild-type gpD alone (10:0) or gpD:HA alone (0:10). The phage particles were then exposed to EDTA (100 mM; lanes marked plus (+)) or left in SM buffer (lanes marked minus (−)) for 15 minutes at 37° C. After this, the phage were added to LE392 *E. coli* host cells and titered by plaque assay. The results show that gpD-deficient phage particles were EDTA-sensitive. Phage particles decorated with gpD:HA alone also remained EDTA-sensitive, indicating that the gpD:HA fusion protein failed to fully coat and stabilize the phage capsid. In contrast, phage capsids decorated with wild-type gpD alone were completely EDTA-resistant, reflecting full occupancy of potential gpD-binding sites and stabilization of the phage capsids. Experiments using mixtures of wild-type gpD and gpD:HA fusion protein revealed that a 4:1 molar ratio of wild-type gpD to gpD:HA was sufficient to generate decorated, mosaic phage particles that were completely resistant to EDTA (and thus contained a full complement of gpD on the phage capsid). This corresponds to approximately 320 copies of wild-type gpD and 80 copies of gpD:HA per phage particle. Mosaic phage that displayed an equimolar ratio of wild-type gpD and gpD:HA fusion protein (one to one (1:1) of 200 copies of each form of gpD per phage capsid) were largely, though not completely, EDTA-resistant. The results, presented in FIG. 6, show that a 4:1 molar ratio of wild-type gpD to gp:HA yielded optimum results in terms of striking a balance between complete decoration of the phage capsid (and resulting EDTA resistance) and permitting a high level of display of HA trimers on the phage surface. Results represent mean values for an experiment that was performed in triplicate; error bars denote the standard deviation. The 1:1 ratio of wild-type gpD to gpD:HA resulted in a slight loss of phage titer upon exposure to EDTA suggesting that some phage did not possess a full complement of gpD molecules.

Figure 5:
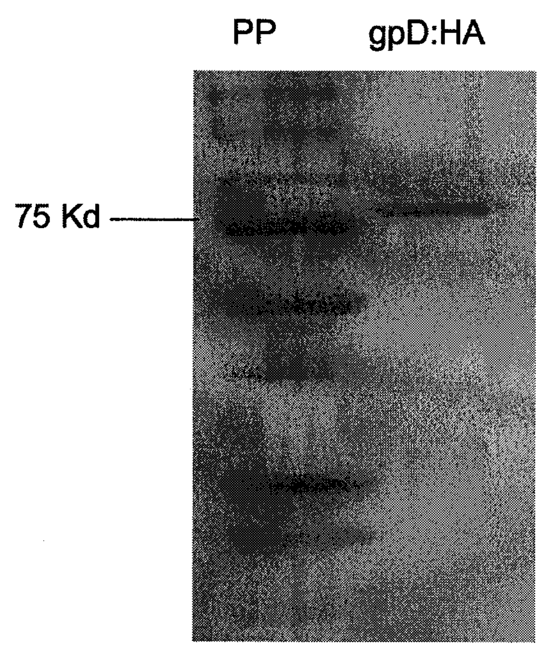
FIG. 5 shows SDS-PAGE analysis of purified, recombinant gpD:HA fusion proteins. Recombinant gpD:HA fusion protein was purified from culture supernatants of *T. ni* insect cells that were infected with a baculovirus vector encoding the corresponding gene cassette. The material was purified by nickel ion chromatography, using the His6 epitope tag on the protein C-terminus. The final elution fraction was dialyzed against SM buffer, and an aliquot was then boiled in SDS sample buffer (containing BME) and loaded onto a 10% SDS-polyacrylamide gel. After electrophoretic separation of the proteins, the material was subjected to Coomassie blue staining. An image of the stained gel is shown. PP denotes molecular weight markers (Precision Plus; Biorad); the size of the 75 kD marker is shown. The monomeric gpD:HA fusion protein was found to migrate with an apparent molecular weight of approximately 75 kD, consistent with what was predicted from in silico analysis. The protein preparation is >95% homogenous, according to this analysis.

Collectively, the data in FIGS. 5 and 6 show that lambda phage particles can be successfully decorated with gpD:glycoprotein fusion proteins, using a simple in vitro method. Therefore, phage particles can be decorated with post-translationally modified proteins such as glycoproteins.

Example 4

Figure 7:
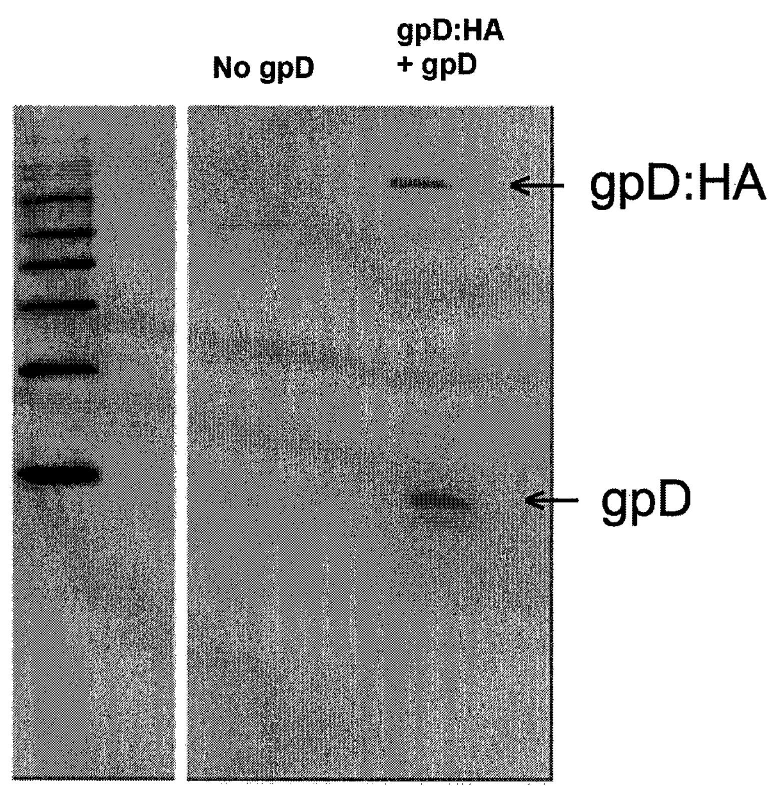
FIG. 7 shows an immunoblot analysis of CsCl density gradient-purified, mosaic phage particles that displayed a 4:1 ratio of wild-type gpD to gpD:HA. gpD-deficient phage were precipitated with PEG overnight, extracted with chloroform and then decorated with a 4:1 ratio of wild-type gpD to gpD:HA. The resulting mosaic phage particles were purified by CsCl density gradient centrifugation and an aliquot of $10^9$ PFU was then subjected to SDS-PAGE and subsequent immunoblot analysis, using a gpD-specific polyclonal antiserum.

Surface Display of 115 Hemagglutin on Lamdba Phage, and Immunogenicity of Phage Particles gpD-deficient phage were precipitated with PEG overnight, extracted with chloroform and then decorated with a 4:1 ratio of wild-type gpD to gpD:HA. The resulting mosaic phage particles were purified by CsCl density gradient centrifugation and an aliquot of $10^9$ PFU was then subjected to SDS-PAGE and subsequent immunoblot analysis, using a gpD-specific polyclonal antiserum. Shown in FIG. 7 is an immunoblot of the purified phage particles, the blot was probed with a polyclonal antiserum directed against gpD. As FIG. 7 shows, the purified mosaic phage particles contained both wild-type gpD and the gpD:HA fusion protein. This indicates that both proteins became incorporated onto the phage capsid.

Figure 8:
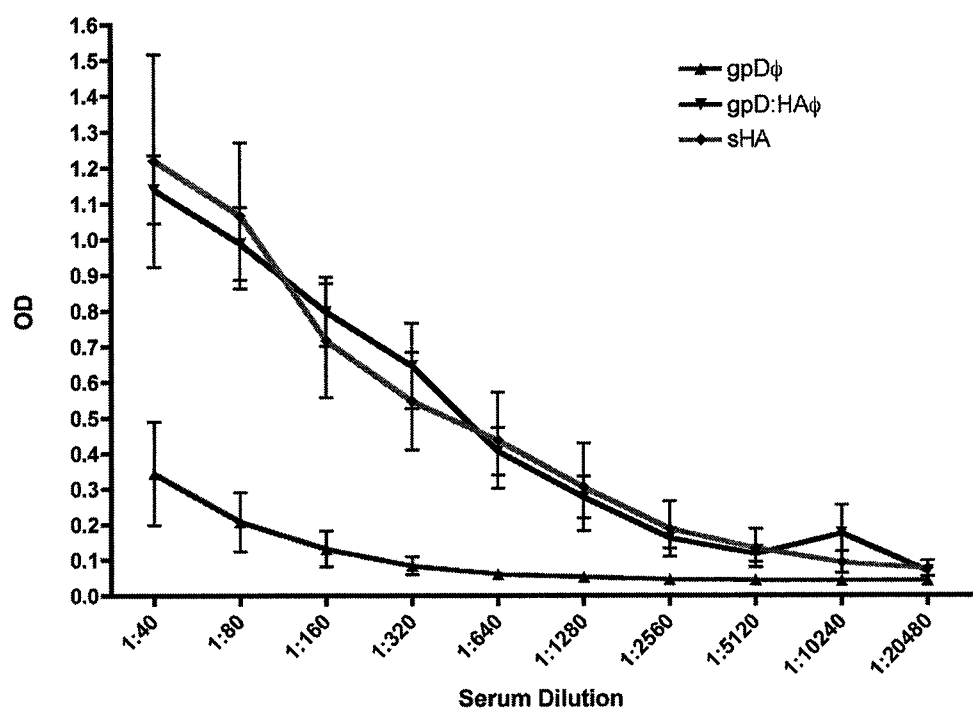
FIG. 8 shows that phage particles displaying gpD:HA (gpD:HA $\phi$) elicited a strong HA-specific IgG antibody response in mice. Groups of four BALB/c mice were immunized with either (i) 10 μg of soluble trimeric H5N1 hemagglutinin ectodomain produced in insect cells (sHA), (ii) $10^{10}$ PFU of gpD:HA $\phi$ (mosaic phage displaying a 4:1 ratio of wild-type gpD to gpD:HA) or (iii) $10^{10}$ PFU of gpD $\phi$ (phage displaying wild-type gpD only). Animals were immunized by the IM route at day 0 and day 14; blood samples were then collected at day 28 for IgG ELISA analysis using plates coated with soluble H5N1 HA.

As shown in FIG. 8, phage particles displaying gpD:HA (gpD:HA 4)) elicited a strong HA-specific IgG antibody response in mice. Groups of four BALB/c mice were immunized with either (i) 10 μg of soluble trimeric H5N1 hemagglutinin ectodomain produced in insect cells (sHA), (ii) $10^{10}$ PFU of gpD:HA (mosaic phage displaying a 4:1 ratio of wild-type gpD to gpD:HA) or (iii) $10^{10}$ PFU of gpD (phage displaying wild-type gpD only). Animals were immunized by the IM route at day 0 and day 14; blood samples were then collected at day 28 for IgG ELISA analysis, using plates coated with soluble H5N1 HA. FIG. 8 shows that the HA-specific IgG antibody response in mice immunized with $10^{10}$ PFU of gpD:HA phage was very similar to that elicited by 10 μg of soluble HA. This is significant because phage inoculum of $10^{10}$ PFU corresponds to only 100 ng of HA. Thus, equivalent immune responses were elicited by soluble HA and a 100-fold lower dose of HA that was displayed on the phage surface.

Example 5

Efficient Production of Trimeric H5 Hemagglutinin in Insect Cells

Expression vectors encoding translational fusions between the major lambda phage coat protein, gpD, and the H5 hemagglutinin (HA) are constructed as follows. These proteins are then be expressed in insect cells, using baculovirus vectors and used to decorate preformed, gpD-deficient phage particles. Phage that codisplay H5 HA plus an immunostimulatory peptide of interest can also be generated.

Hemagglutinins from both the 1918 human influenza A virus and a highly pathogenic Vietnamese H5N1 virus can be used to construct the fusion proteins. The constructs can also contain an exogenous trimerization motif (the fibritin foldon), a His 6 tag for purification and a thrombin cleavage site (all on the C-terminus of the protein). The fusion protein can also be fused in-frame to an insect cell signal peptide (present in plasmid pAcGP67A [BD Pharmingen]), which contains the following additional residues at its C-terminus: SGRLVPRG-SPGSGYIPEAPRDGQAWRKDGEWVLLST-FLGHHHHHH* (SEQ ID NO. 27). The sequence in italics is the thrombin site, the foldon sequence is underlined, and the His-tag is indicated in bold type. The construct can also be codon-optimized to enhance protein production in insect cells. The sequences encoding this cassette can be fused to a sequences encoding gpD, optionally together with a flexible linker/spacer peptide, to generate the following protein fusion product:

PROMOTER->(Secretion signal from pAcGP67A)-(gD)-(spacer)-(H5 HA ecto)-Tags-[STOP]

Example 6

Codon Optimization of Fusion Proteins

Insect cell codon-optimized versions of the gene encoding the gpD:HA fusion protein can be generated as follows. Briefly, codon optimization refers to the alteration of gene sequences, to make codon usage match the available tRNA pool within the cell/species of interest. Codon optimization dramatically enhances protein expression from a wide range of virus genes.

Figure 9A:
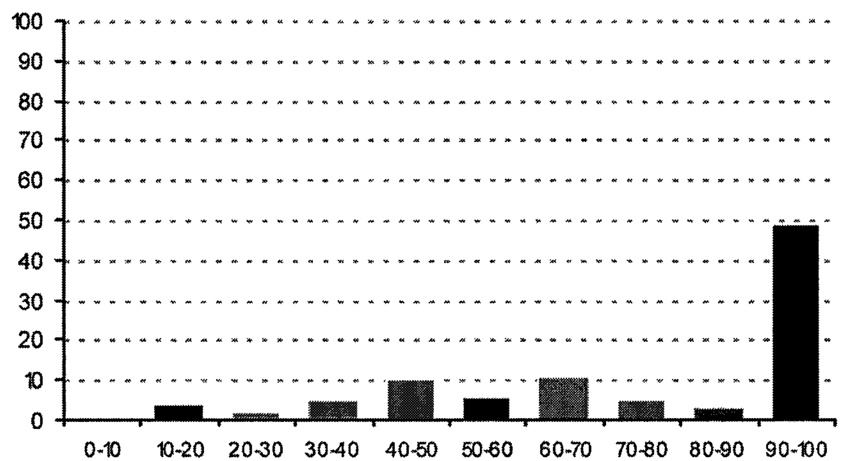
FIGS. 9A and 9B are histograms showing the percentage of sequence codons, which fall into a certain quality class. The quality value of the most often used codon for a given amino acid in the desired expression system is set to 100; the remaining codons are scaled accordingly.
Figure 9B:
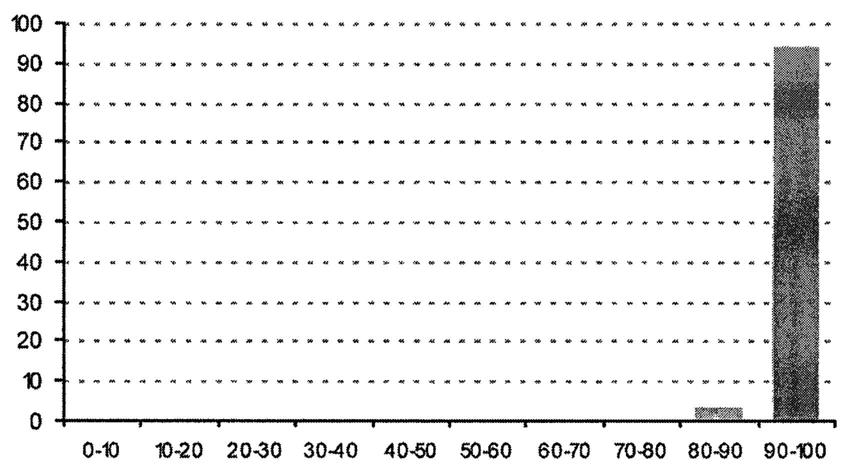

Analysis of the H5 HA gene revealed that it uses codons that are rare in insect cells. It also contains several cis-acting motifs that may hamper expression in insect cells, including cryptic splice sites and potential RNA instability motifs. The codon usage pattern for the wild-type gpD:HA fusion gene (unmodified) is shown in FIGS. 9A and 9B.

Example 7

The Majority of Normal Adults do not have Pre-Existing Humoral Immunity to Bacteriophage Lambda A large panel of normal sera from adult subjects who were volunteers in recent HIV vaccine trials were obtained from the HIV Vaccine Trials Network and Duke University. These sera were then screened for antibody reactivity to lambda phage, by testing for the presence of IgG antibodies directed against the immunodominant major phage coat protein, gpD.

GpD protein was expressed as a His6-tagged recombinant molecule in *E. coli* host cells and then purified by metal ion chromatography to approximately 90% homogeneity (as assessed by Coomassie blue staining of SDS-PAGE gels loaded with the final column eluate). This material was then used to set up an ELISA assay to identify gpD specific antibodies in human sera. For this analysis, ELISA plates were first coated with a gpD-specific rabbit polyclonal antiserum, prior to addition of purified recombinant gpD protein and subsequent washing. Two-fold serial dilutions of the test sera (starting at 1:20, and going down to 1:160) were then added, and allowed to react with the immobilized gpD. After an additional wash step, bound human antibodies were detected using an HRP-conjugated, affinity-purified polyclonal antiserum directed against human IgG. Positive controls included a rabbit polyclonal antiserum directed against gpD as well as serum from a mouse that had been immunized with intact lambda phage particles; in both cases, bound antibody was detected using a species-appropriate detection antibody (i.e., anti-rabbit or anti-mouse, as appropriate). Negative controls included (i) no primary antibody (i.e., enzyme-conjugated detection antibody alone), and (ii) sera from RAG mice (expected to be devoid of IgG antibodies). Results for the panel of test sera (n=87) are summarized in Table 1.

As noted in Table 1, a few of the human sera appeared to have low titers of gpD-specific antibodies (8 out of 87 analyzed), reflected by ELISA reactivity that was just above the cutoff of the assay. To assess whether these results were the result of background reactivity against residual impurities present in the recombinant gpD preparation, or the result of bona fide reactivity to gpD itself, we conducted an immunoblot analysis using the entire serum panel. For this analysis, the His6-tagged recombinant gpD protein described above was separated by SDS-PAGE, and transferred to a nitrocellulose membrane. Membrane strips were then prepared and reacted with human serum samples, diluted 1:20 in blocking buffer (5% skim milk in PBS). Bound antibodies were detected with the anti-human IgG antibody described above, and visualized using the ECL system (Amersham Pharmacia). The same positive and negative control sera described in the preceding paragraph were also used in this analysis, together with appropriate detection antibodies. All of the control sera gave the expected results (i.e., positive control sera specifically recognized a band at the expected molecular weight for gpD, while negative control sera failed to yield such reactivity). Importantly, none of the human sera contained antibodies that reacted specifically with gpD. These data suggest that the vast majority of normal adults do not have pre-existing humoral immunity to bacteriophage lambda.

TABLE 1

Reactivity of human sera to the lambda phage coat protein, gpD

| Sera | Endpoint ELISA Titer* (n = No. of sera) | Immunoblot** (n = No. of sera) |
|---|---|---|
| Pos. control mouse serum (phage-immunized BALB/c animal)*** | >1:160 | Pos. |
| Neg. control mouse serum (RAG animal) | Neg. | Neg. |
| Human sera (vaccine study volunteers) | Neg. (n = 79)<br>1:20 (n = 3)<br>1:40 (n = 3)<br>1:160 (n = 2) | Neg. (n = 87) |

*Negative ELISA titer denotes a titer that was below the assay cutoff, when measured with a 1:20 dilution of serum (the highest concentration tested).

**Reactivity on immunoblot is defined as the presence or absence of reactivity to a band with the expected molecular weight of His6-tagged gpD (approx. 12-15 kDa)

***Mouse serum was detected with an anti-mouse IgG; human sera were detected with an anti-human IgG

What is claimed is:

1. A method for displaying a post-translationally modified polypeptide on the surface of a phage comprising (a) providing a mammalian host cell comprising one or more expression vectors encoding a plurality of fusion polypeptides, wherein each expression vector comprises a nucleic acid encoding a fusion polypeptide and wherein the fusion polypeptide comprises a surface polypeptide and a heterologous polypeptide capable of being post-translationally modified;

(b) culturing the mammalian host cell under conditions that allow the fusion polypeptides to be expressed and that allow the heterologous polypeptides to be post-translationally modified;

(c) isolating the fusion polypeptides; and d) incubating the phage with the fusion polypeptides wherein the cell is transformed with one or more expression vectors encoding a plurality of fusion polypeptides and wherein the cell expresses a first fusion polypeptide comprising SF162 Env and gpV or gpD and a second fusion polypeptide comprising YU2 Env and gpV or gpD.

* * * * *